United States Patent [19]
Markowitz et al.

[11] Patent Number: 5,866,323
[45] Date of Patent: Feb. 2, 1999

[54] CANCER DIAGNOSIS PROGNOSIS AND THERAPY BASED ON MUTATION OF RECEPTORS FOR TRANSFORMING GROWTH FACTOR β AND HOMOLOGOUS GROWTH CONTROLLING FACTORS

[75] Inventors: Sanford D. Markowitz, Shaker Heights; Michael G. Brattain, Maumee; James K. V. Willson, Shaker Heights, all of Ohio

[73] Assignees: Case Western Reserve University, Cleveland; Medical College of Ohio, Toledo, both of Ohio

[21] Appl. No.: 445,520

[22] Filed: May 22, 1995

Related U.S. Application Data

[63] Continuation-in-part of Ser. No. 417,867, Apr. 7, 1995, abandoned.

[51] Int. Cl.[6] .......................... C12N 15/00; G01N 33/567
[52] U.S. Cl. ................. 435/6; 435/7.1; 435/7.2; 435/7.21; 435/7.23; 436/503; 436/811
[58] Field of Search ...................... 530/387.1; 536/23.5; 435/6, 7.1, 7.2, 7.21, 7.23; 436/501–504, 811

[56] References Cited

U.S. PATENT DOCUMENTS

| | | | |
|---|---|---|---|
| 4,399,216 | 8/1983 | Axel et al. | 435/6 |
| 4,446,128 | 5/1984 | Baschang et al. | 424/88 |
| 4,920,209 | 4/1990 | Davis et al. | 435/235 |
| 5,166,059 | 11/1992 | Pastan et al. | 435/69.7 |

FOREIGN PATENT DOCUMENTS

| | | |
|---|---|---|
| WO9220793 | 11/1992 | WIPO . |
| WO9309228 | 5/1993 | WIPO . |
| WO9409815 | 5/1994 | WIPO . |

OTHER PUBLICATIONS

Hasegawa, et al., "Characterization of a Human Hepatoma Cell Line with Acquired Resistance to Growth Inhibition by Transforming Growth Factor Beta 1 (TGF–β1)", *In–Vitro Cell Dev. Biol.*, vol. 31a, No. 1, Jan. 1995, pp. 55–61.
Brand, et al., "A dominant–negative Receptor for Type β Transforming Growth Factors Created by Deletion of the Kinase Domain:", *J. Biol. Chem.* vol. 266, No. 14, May 1991, pp. 9018–9112.
Parsons, et al., "Microsatellite Instability and Mutations of the Transforming Growth Factor β Type II Receptor Gene in Colorectal Cancer", *Cancer Res.*, vol. 55, Dec. 1995, pp. 5548–5550.
Myeroff, et al., "A Transforming Growth Factor β Receptor Type II Gene Mutation Common in Colon and Gastric but Rare in Endometrial Cancers with Microsatellite Instability", *Cancer Res.*, vol. 55, Dec. 1995, pp. 5545–5547.
Wang, et al., "Demonstration That Mutation of the Type II Transforming Growth Factor β Receptor Inactivates its Tumor Suppressor Activity in Replication Error–positive Colon Carcinoma Cells", *J. Biol. Chem.*, vol. 270, No. 37, Sep. 1995, pp. 22044–22049.

Brand, et al., :Inactive Type II and Type I Receptors for TGFβ Are Dominant Inhibitors of TGFβ–dependent Transcription, *J. Biol, Chem.*, vol. 270, No. 14, Apr. 1995, pp. 8274–8284.
Altered Expression of Transmorming Growth Factor–α and Transforming Growth Factor–β Autocrine Loops in Cancer Cells:, M.G. Brattain et al., *Advanced in Molecular and Cell Biology*, vol. 7, pp. 35–59, 1993.
"Inactivation of the Type II TGF–β Receptor in Colon Cancer Cells with Microsatellite Instability", S. Markowitz et al., *Science*, vol. 268, Jun. 1995.
"DNA Repair Defect Tied to Mutated TGF–β Receptor Gene", Jean Marx, *Science*, vol. 268, pp. 1276–1277, Jun. 1995.
"Loss of Receptors for Transforming Growth Factor β in Human T–cell Malignancies", M. Kadin et al, *Pro. Natl. Acad. Sci., USA*, vol. 91, pp. 6002–6006, Jun. 1994.
"Clues to the Pathogenesis of Familial Colorectal Cancer", Lauri A. Aaltonen, et al, *Science*, vol. 260, pp. 812–815, May 1993.
"Transforming Growth Factor $β_1$ Can Induce Estrogen–Independent Tumorigenicity of Human Breast Cancer Cells in Athymic Mice[1]", Carlos L. Arteaga, et al, *Cell Growth & Differentiation*, vol. 4, pp. 193–201, Mar. 1993.
"TCF–β Expression in the Human Colon: Differential Immunostaining Along Crypt Epithelium", A. Avery et al, *Brit. J. Cancer*, vol. 68, p. 137.
"High–Resolution in Situ Hybridization Histochemistry", Frank Baldino, Jr., et al, *Methods in Enzymology*, vol. 168, pp. 761–777.
"A Transforming Growth Factor β Type 1 Receptor That Signals to Activate Gene Expression", Craig H. Bassing, *Science*, vol. 263, pp. 87–89, Jan. 1994.
"$β_2$–Microglobulin Gene Mutations: A Study of Established Colorectal Cell Lines and Fresh Tumors", D.C. Bicknell, et al, *Proc. Natl. Acad. Sci. USA*, vol. 91, pp. 4751–4755, May 1994.
"Transforming Growth Factor–β Inhibition of Epithelial Cell Proliferation Linked to the Expression of a 53–kDa Membrane Receptor", Frederick T. Boyd et al, *The Journal of Biological Chemistry*, vol. 264, No. 4, pp. 2272–2278, Feb. 1989.
"Growth Factor Balance and Tumor Progression", Michael G. Brattain, et al, *Current Opinion in Oncology*, vol. 6, pp. 77–81, 1994.
"Mutation in the DNA Mismatch Repair Gene Homologue hMLH 1 is Associated with Hereditary Non–Polyposis Colon Cancer", C. Bronner et al, *Nature*, vol. 368, pp. 258–261, Mar. 1994.

(List continued on next page.)

*Primary Examiner*—Marianne P. Allen
*Attorney, Agent, or Firm*—Baker & Botts LLP

[57] ABSTRACT

This invention is based on the discovery that the type II TGF-β receptor (RII) is a cancer suppressor gene which is genetically inactivated (mutated) in approximately 25% of colon cancers, including nearly all colon cancers of the class identified as mutator/microsatellite instability/RER. Methods are provided for detecting inactivation of RII for use in cancer diagnosis or prognosis.

20 Claims, 5 Drawing Sheets

OTHER PUBLICATIONS

"Immune Response to p53 is Dependent Upon p53/HSP70 Complexes in Breast Cancers", Andrew M. Davidoff, *Proc. Natl. Acad. Sci. USA*, vol. 89, pp. 3439–3442, Apr. 1992.

"Total Synthesis of a Human Leukocyte Interferon Gene", Michael D. Edge, et al, *Nature*, vol. 292, pp. 756–762, Aug. 1981.

"Nonradioactive Methods of in Situ Hybridization: Visualization of Neuroendocrine mRNA", P.C. Emson et al, *Methods of Enzymology*, vol. 168, pp. 753–760.

"Increased Mutation Rate at the hprt Locus Accompanies Microsatellite Instability in Colon Cancer", James R. Eshleman, *Oncogene*, vol. 10, pp. 33–37, 1995.

"Microsatellite Instability in Inherited and Sporadic Neoplasms", James R. Eshleman, *Current Opinion in Oncology*, vol. 7, pp. 83–89, 1995.

"Development of Resistance Mechanism to the Growth–Inhibitory Effects of Transforming Growth Factor–β During Tumor Progression", Jorge Filmus, et al, *Current Opinion in Oncology*, vol. 5, pp. 123–129, 1993.

"The Human Mutator Gene Homolog MSH2 and Its Association with Hereditary Nonpolyposis Colon Cancer", Richard Fishel, et al, *Cell*, vol. 75, pp. 1027–1038, Dec. 1993.

"Detection of p53 Gene Mutations in Rat Hepatocellular Carcinoma Cell Lines by Denaturing Gradient Gel Electrophoresis", Ikue Fukuda, et al, *Molecular Carcinogensis*, vol. 7, pp. 257–262, 1993.

"Inhibition of Growth by Transforming Growth Factor–β following Fusion of Two Nonresponsive Human Carcinoma Cell Lines", Andrew G. Geiser, et al, *The Journal of Biological Chemistry*, vol. 267, No. 4, pp. 2588–2593, Feb. 1992.

"Loss of Expression of Transforming Growth Factor β in Skin and Skin Tumors is Associated with Hyperproliferation and a High Risk for Malignant Conversion", Adam B. Glick, et al, *Pro. Natl. Acad. Sci. USA*, vol. 90, pp. 6076–6080, Jul. 1993.

"Differential Sensitivity of Subclasses of Human Colon Carcinoma Cell Lines to the Growth Inhibitory Effects of Transforming Growth Factor–β1", Naseema S. Hoosein, et al, *Experimental Cell Research*, vol. 181, pp. 442–453, 1989.

"Ubiquitous Somatic Mutations in Simple Repeated Sequences Reveal a New Mechanism for Colonic Carcinogensis", Yurij Ionov, et al, *Nature*, vol. 363, pp. 558–561, Jun. 1993.

"Detection of Point Mutations by SSCP of PCR–Amplified DNA After Endonuclease Digestion", Iwanhana, et al, *Biotechniques*, vol. 12, No. 1, 64–66, 1992.

"Chemical Synthesis of Biologically Active Gene for Human Immune Interferon–γ", Ernest Jay, et al, *The Journal of Biological Chemistry*, vol. 259, No. 10, pp. 6311–6317, May 1984.

"Clinical and Pathological Characteristics of Sporadic Colorectal Carcinomas with DNA Replication Errors in Microsatellite Sequences", Hoguen Kim, et al, *American Journal of Pathology*, vol. 145, pp. 148–156, Jul. 1964.

"Absence of TGF–β Receptors and Growth Inhibitory Responses in Retinoblastoma Cells", Adi Kimchi, et al, *Science*, vol. 240, pp. 196–199.

"Derivation of Specific Antibody–Producing Tissue Culture and Tumor Lines by Cell Fusion", G. Kohler et al, *Eur. J. Immunol.*, vol. 6, pp. 511–519, 1976.

"Activation of ras Oncogenes Preceding the Onset of Neoplasia", Ramesh Kumar, et al, *Science*, vol. 248, pp. 1101–1104, Jun. 1990.

"Activation of H–ras Oncogenes in Preneoplastic Mouse Mammary Tissues", Ramesh Kumar, et al, *Oncogene*, vol. 5, pp. 1271–1277.

"Clinical Implications of the p53 Tumor–Suppressor Gene", Curtis C. Harris, et al, *The New England Journal of Medicine*, vol. 329, No. 18, pp. 1318–1327, Oct. 1993.

"Loss of Transforming Growth Factor $\beta_1$ and Its Effects on the Growth of EBV–Transformed Human B Cells", Ashok Kumar, et al, *The Journal of Immunology*, vol. 147, No. 3, pp. 998–1006.

"Slippery DNA and Diseases", Thomas A. Kunkel, *Nature*, vol. 365, pp. 207–208, Sep. 1993.

"Concomitant Loss of Transforming Growth Factor (TGF)–β Receptor Types I and II in TGF–β–resistant Cell Mutants Implicates Both Receptor Types in Signal Transduction", Marikki Laiho, et al, *The Journal of Biological Chemistry*, vol. 265, No. 30, pp. 18518–18524, Oct. 1990.

"Accumulation of Multiple Mutations in Tumour Suppressor Genes During Colorectal Tumorigenesis in HNPCC Patients", Vladmir Lazar, et al, *Human Molecular Genetics*, vol. 3, No. 12, pp. 2257–2260, 1994.

"Mutations of a mutS Homolog in Hereditary Nonpolyposis Colorectal Cancer", Frederick S. Leach, et al, *Cell*, vol. 75, pp. 1215–1225, Dec. 1993.

"Transcriptional Repression of Eukaryotic Promoters", Michael Levine, et al, *Cell*, vol. 59, pp. 405–408, Nov. 1989.

"Expression Cloning of the TGF–β Type II Receptor, a Functional Transmembrane Serine/Threonine Kinase", Herbert Y. Lin, et al, *Cell*, vol. 68, pp. 775–785, Feb. 21, 1992.

"Mismatch Repair Gene Defects in Sporadic Colorectal Cancers with Microsatellite Instability", Bo Liu, et al, *Nature Genetics*, vol. 9, pp. 48–55, Jan. 1995.

"Betaglycan Presents Ligand to the TGF–β Signaling Receptor", Fernando Lopez–Casillas, et al, *Cell*, vol. 73, pp. 1435–1444, Jul. 1993.

"Genomic Instability in Colorectal Cancer: Relationship to Clinicopathological Variables and Family History", Ragnhild A. Lothe, et al, *Cancer Research*, vol. 53, pp. 5849–5852, Dec. 1993.

"Differential Sensitivity of Human Colonic Adenoma and Carcinoma Cells to Transforming Growth Factor β (TGF–β): Conversion of an Adenoma Cell Line to a Tumorigenic Phenotype is Accompanied by a Reduced Response to the Inhibitory Effects of TGF–β", Anna M. Manning, et al, *Oncogene*, vol. 6, pp. 1474–1476, 1991.

"A Benign Cultured Colon Adenoma Bears Three Genetically Altered Colon Cancer Oncogenes, but Progresses to Tumorigenicity and Transforming Growth Factor–Beta Independence Without Inactivating the p53 Tumor Suppressor Gene", Sanford D. Markowitz, et al, *J. Clin. Invest.*, vol. 93, pp. 1005–1013, Mar. 1994.

"The Transforming Growth Factor–β Family", Joan Massague, *Annu. Rev. Cell Biol.*, vol. 6, pp. 597–641, 1990.

"TGF–β Receptors and TGF–β Binding Proteoglycans: Recent Progress in Identifying Their Functional Properties", Joan Massague, et al, *Annals New York Academy of Sciences*, vol. 593, pp. 59–73.

"Responsiveness to Transforming Growth Factor–β (TGF–β) Restored by Genetic Complementation Between Cells Defective in TGF–β Receptors I and II", Marikki Laiho, et al, *The Journal of Biological Chemistry*, vol. 266, No. 14, pp. 9108–9112, May 1991.

"The TGF–β Family and Its Composite Receptors", Joan Massague, et al, *Trends in Cell Biology*, vol. 4, pp. 173–178, May 1994.

"α–Inhibin is a Tumour–Suppressor Gene with Gonadal Specificity in Mice", Martin M. Matzuk, et al, *Nature*, vol. 360, pp. 313–319, Nov. 1992.

"Functional Analysis of Activins During Mammalian Development", Martin M. Matzuk, et al, *Nature*, vol. 374, pp. 354–356, Mar. 1995.

"Different Phenotypes for Mice Deficient in Either Activins or Activin Receptor Type II", Martin M. Matzuk, et al, *Nature*, vol. 374, pp. 356–360, Mar. 1995.

"TGF–β Stimulation and Inhibition of Cell Proliferation: New Mechanistic Insights", Harold L. Moses, et al, *Cell*, vol. 63, pp. 245–247, Oct. 1990.

"The Transforming Growth Factor βReceptors Types I, II, and III Form Hetero–oligomeric Complexes in the Presence of Ligand", Aristidis Moustakas, et al, *The Journal of Biological Chemistry*, vol. 268, No. 30, pp. 22215–22218, Oct. 1993.

"Specific Synthesis of DNA in Vitro via a Polymerase–Catalyzed Chain Reaction", Kary B. Mullis et al, *Methods of Enzymology*, vol. 155, pp. 335–350.

"Production of Transforming Growth Factor–Beta Activity by Ki–1 Positive Lymphoma Cells and Analysis of Its Role in the Regulation of Ki–1 Positive Lymphoma Growth", Samuel R. Newcom, et al, *American Journal of Pathology*, vol. 131, No. 3, Jun. 1988.

"Mutations of two PMS Homologyes in Hereditary Nonpolyposis Colon Cancer", Nicholas C. Nicolades, et al, *Nature*, vol. 371, pp. 75–80, Sep. 1994.

"Rapid and Sensitive Detection of Point Mutations and DNA Polymorphisms Using the Polymerase Chain Reaction", Masato Orita, et al, *Genomics*, vol. 5, pp. 874–879, 1989.

"Mutation of a mutL Homolog in Hereditary Colon Cancer", Nickolas Papdopoulos, et al, *Science*, vol. 263, pp. 1625–1629, Mar. 1994.

"Genetic Changes in the Transforming Growth Factor β (TGF–β) Type II Receptor Gene in Human Gastric Cancer Cells: Correlation with Sensitivity to Growth Inhibition by TGF–β", Keunchil Park, et al, *Proc. Natl. Acad. Sci. USA*, vol. 91, pp. 8772–8776, Sep. 1994.

"Hypermutability and Mismatch Repair Deficiency in RER+ Tumor Cells", Ramon Parsons, et al, *Cell*, vol. 75, pp. 1227–1236, Dec. 1993.

"The Transforming Growth Factor–βs", A.B. Roberts, et al, *Handbook of Experimental Pharmacology*, pp. 419–472.

"Genes with Triplet Repeats: Candidate Mediators of Neuropsychiatric Disorders", Christopher A. Ross, et al, *TINS*, vol. 16, No. 7, pp. 254–259, 1993.

"The Immune Response to p53 in Breast Cancer Patients is Directed Against Immunodominant Epitopes Unrelated to the Mutational Hot Spot", Beata Schlichtoholz, et al, *Cancer Research*, vol. 52, pp. 6380–6384, Nov. 1992.

"Targeted Disruption of the Mouse Transforming Growth Factor–β1 Gene Results in Multifocal Inflammatory Disease", Marcia M. Shull, et al, *Nature*, vol. 359, pp. 693–699, Oct. 1992.

"Growth Inhibition of a Human Lymphoma Cell Line: Induction of a Transforming Growth Factor–β–Mediated Autocrine Negative Loop By Phorbol Myristate Acetate", Garwin K. Sing, et al, *Cell Growth & Differentiation*, vol. 7, pp. 549–557, Nov. 1990.

"PCR Amplification of Specific Alleles (PASA) is a General Method for Rapidly Detecting Known Single–Base Changes", Steve S. Sommer, et al, *BioTechniques*, vol. 12, No. 1, pp. 82–87, 1992.

"Destabilization of Tracts of Simple Repetitive DNA in Yeast by Mutations Affecting DNA Mismatch Repair", Micheline Strand, et al, *Nature*, vol. 365, pp. 274–276, Sep. 1993.

"Specific Patterns of Oncogene Activation in Transplacentally Induced Tumors", Saraswati Sukumar, et al, *Proc. Natl. Acad. Sci. USA*, vol. 87, pp. 718–722, Jan. 1990.

"Frequent Activation of the Ki–ras Oncogene at Codon 12 in N–Methyl–N–Nitrosourea–Induced Rat Prostate Adenocarcinomas and Neurogenic Sarcomas", Saraswati Sukumar, et al, *Molecular Carcinogenesis*, vol. 4, pp. 362–368, 1991.

"Expression of Tranforming Growth Factor β Type II Receptor Leads to Reduced Malignancy in Human Breast Cancer MCF-7 Cells", LuZhe Sun, et al, *The Journal of Biological Chemistry*, vol. 269, No. 42, pp. 26449–26455, 1994.

"Microsatellite Instability in Cancer of the Proximal Colon", S.N. Thibodeau, et al, *Science*, vol. 260, pp. 816–819, May 1993.

"Amplifying Genes: PCR and Its Alternatives", Jennifer Van Brunt, *Bio/Technology*, vol. 8, pp. 291–294, Apr. 1990.

"In Situ cDNA:mRNA Hybridization: Development of a Technique to Measure mRNA Levels in Individual Cells", Josiah N. Wilcox, et al, *Methods in Enzymology*, vol. 124, pp. 510–533.

"Development of Antibodies Against p53 in Lung Cancer Patients Appears to be Dependent on the Type of p53 Mutation", Stefan F. Winter, et al, *Cancer Research*, vol. 52, pp. 4168–4174, Aug. 1992.

"TGF–β Signals Through a Hetermeric Protein Kinase Receptor Complex", Jeffrey L. Wrana, et al, *Cell*, vol. 71, pp. 1003–1014, Dec. 1992.

"Repression of Autocrine Transforming Growth Factor $β_1$ and $β^2$ in Quiescent CBS Colon Carcinoma Cells Leads to Progression of Tumorigenic Properties", S.P. Wu, et al, *Cell Growth & Differentiation*, vol. 4, pp. 115–123, Feb. 1993.

"TGF–$β_1$ Is an Autocrine–negative Growth Regulator of Human Colon Carcinoma FET Cells in Vivo as Revealed by Transfection of an Antisense Expression Vector", Shaoping Wu, et al, *The Journal of Cell Biology*, vol. 116, pp. 187–195, 1992.

X axis displays colon cancer cell lines

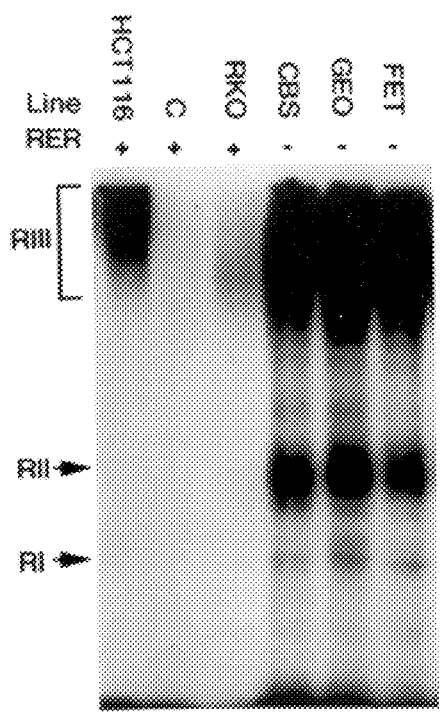
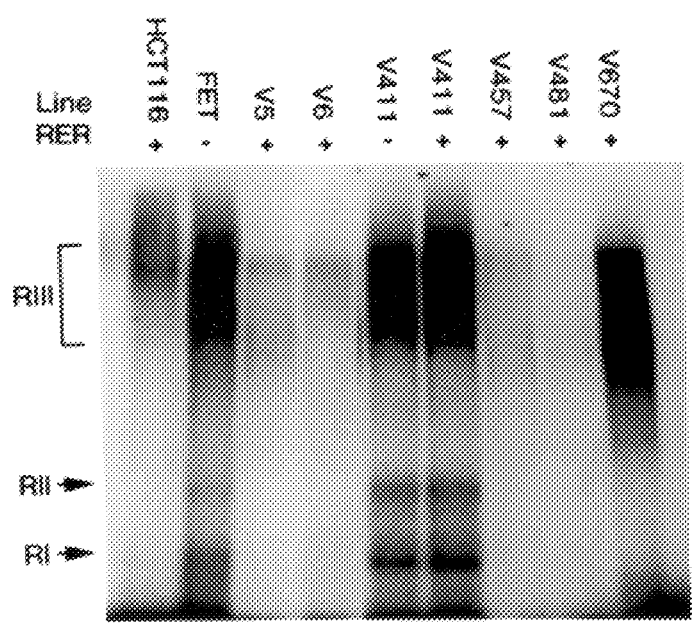
FIG. 3A                  FIG. 3B

CANCER DIAGNOSIS PROGNOSIS AND THERAPY BASED ON MUTATION OF RECEPTORS FOR TRANSFORMING GROWTH FACTOR β AND HOMOLOGOUS GROWTH CONTROLLING FACTORS

This application is a Continuation-In-Part of U.S. Ser. No. 08/417,867, filed Apr. 7, 1995, now abandoned which is incorporated herein in its entirety by reference.

The work leading to this invention was supported in part by Grant Nos. CA38173, CA50457, CA51504, CA57208 and CA51183 from the National Institutes of Health. The U.S. Government retains certain rights in this invention.

BACKGROUND OF THE INVENTION

1. Field of the Invention

This invention is concerned with diagnostic methods which assist in classification of tumors by phenotype and with therapeutic intervention tailored to particular tumor phenotypes. In particular this invention concerns mutant forms of type II receptors (RII) for transforming growth factor beta (TGF-β) which inactivate growth suppression by TGF-β, methods for detecting inactivation of TGF-β RII receptor and therapeutic methods for restoring tumor suppression by restoring RII function.

2. Review of Related Art

TGF-β inhibits growth of multiple epithelial cell types, and loss of this negative regulation is thought to contribute to tumor development (Roberts, et al., 1990, In *Peptide Growth Factors and Their Receptors. Handbook of Experimental Pharmacology*, A. Roberts and M. Sporn, Eds., (Springer-Verlag, Heidelberg) pp. 419–472; Massagué, J., 1990, *Annu. Rev. Cell Biol*, 6:597; Moses, et al., 1990, Cell, 63:247; Filmus, et al., 1993, *Curr. Opin. Oncol.*, 5:123; Markowitz, S., et al., 1994, *J. Clin. Invest.*, 93:1005; Wu, S., et al., 1992, *J. Cell. Biol.*, 116:187; Wu, S., et al., 1993, *Cell Growth Differ.*, 4:115; Park, J., et al., 1994, *Proc. Natl. Acad. Sci. U.S.A.*, 91:8772; Manning, et al., 1991, *Oncogene*, 6:1471; Hoosein, N., et al., 1989, *Exp. Cell Res.*, 181:442; Geiser, et al., 1992, *J. Biol. Chem.*, 267:2588). Previous studies have demonstrated that TGF-β suppresses growth of certain cancer cell lines, that antisense inhibition of TGF-β enhances the tumorigenicity of weakly tumorigenic cancer cell lines, and that certain tumor cells can become unresponsive to TGF-β (Markowitz, S., et al., 1994, *J. Clin. Invest.*, 93:1005; Wu, S., et al., 1992, *J. Cell. Biol.*, 116:187; Wu, S., et al., 1993, *Cell Growth Differ.*, 4:115; Park, J., et al., 1994, *Proc. Natl. Acad. Sci. U.S.A.*, 91:8772; Manning, et al., 1991, Oncogene, 6:1471; Hoosein, N., et al., 1989, *Exp. Cell Res.*, 181:442; Geiser, et al., 1992, *J. Biol. Chem.*, 267:2588).

The TGF-β growth inhibitory signal is transduced through two receptors, type I (RI) and type II (RII) which function as a heteromeric complex (Lin, et al., 1992, *Cell*, 68:775; Moustakas, A., et al., 1993, *J. Biol. Chem.*, 268:22215; Wrana, J., et al., 1992, *Cell*, 71:1003).

SUMMARY OF THE INVENTION

It is an object of this invention to provide a method for diagnosis or prognosis of cancer by detection of the absence of functional TGFβ receptor RII in cells of a patient.

It is another object of this invention to provide a nucleotide sequence encoding a mutant form of RII, to provide mutant RII protein and to provide antibodies specifically immunoreactive with mutant RII.

It is yet another object of this invention to provide therapeutic methods for treating tumors having inactive RII by replacement gene therapy.

It is still another object of this invention to provide immunogenic compositions which elicit antibodies specifically reactive with cells expressing mutant forms of RII.

These and other objects are provided by one or more of the following embodiments.

In one embodiment, this invention provides a diagnostic method to aid in predicting prognosis of a colon cancer patient comprising determining the quantity of functional type II receptor for TGFβ (RII) in cells from tumor tissue of the patient, and comparing the quantity of RII in tumor cells to the quantity of RII in non-neoplastic cells of the patient, reduced RII in the tumor cells being indicative of altered prognosis. In a particular embodiment, this invention provides a screening method to aid in classifying tumor cell phenotype in a patient comprising determining the presence or absence of functional RI receptor for TGFβ in tumor tissue from the patient, the absence of functional RII being indicative of carcinoma with replication errors (RER phenotype). The screening method is preferably applied to tumor tissue from endometrial cancer, ovarian cancer, gastric cancer, or pancreatic cancer, most preferably to colon cancer.

In another embodiment, this invention provides a method to aid in diagnosing cancer in a patient comprising detecting, in the patient, a non-functional mutant form of a growth regulatory gene, wherein the growth regulatory gene encodes a type II receptor which is a member of a family of serine/threonine receptors which bind members of a family of TGFβ-like factors or the wild-type of the growth regulatory gene contains repetitive DNA sequence motifs in the coding region, presence of the non-functional mutant form of the growth-regulatory gene being indicative of tumor tissue or precancerous lesions in the patient. In a particular embodiment, this invention provides a screening method to aid in diagnosing cancer in a patient comprising determining the presence or absence of functional RII receptor for TGFβ in tissue from the patient, the absence of functional RII being indicative of tumor tissue or precancerous lesions in the patient. In a particular embodiment, the screening method comprises determining the presence or absence of mutant forms of RII receptor for TGFβ, preferably mutant forms of RII encoded by RII cDNA altered by a mutation selected from the group consisting of a two base pair insertion of GT which occurs in a six base pair repeat sequence GTGTGT at codons 1931–1936 of the normal RII sequence, deletion of one A base pair from a ten base pair poly A sequence at codons 709 to 718 of the normal RII sequence, deletion of two A base pairs from a ten base pair poly A sequence at codons 709 to 718 of the normal RII sequence, and addition of one or two A base pairs into the ten base pair poly A sequence at codons 709–718 of the normal RII sequence. Mutant RII may be detected by immunoassay or by assays sensitive to DNA or RNA sequence. The assays are performed on samples from the patient which may be samples from tumor or normal tissue or samples of biological fluids, including serum, plasma, effusions, ascites, urine, stool, cerebrospinal fluid, semen, breast aspirates and fluids of ovarian origin. Alternatively, the presence of mutant RII in a patient may be detected by immunoassays which detect, in the patient, production of an antibody response aimed against either the RII mutation or, due to breaking of immune tolerance, against other epitopes on the native RII protein.

In yet another embodiment, this invention provides a method to aid in diagnosing cancer in a patient comprising detecting a mutant RII receptor for TGFβ in a sample of biological fluid from the patient. The mutant form of RII may be detected directly or it may be detected indirectly by detecting antibody immunologically reactive with the mutant form of RII in a sample of biological fluid from the patient. The antibody immunologically reactive with mutant RII receptor for TGFβ may also be immunologically reactive with wild type RII receptor.

In another embodiment, this invention provides a heterologous polynucleotide, either DNA or RNA, comprising a nucleotide sequence encoding a mutant form of TGFβ receptor RII, the mutation being addition or deletion of one or two adenosine base-pairs from a ten base-pair polyadenosine sequence at codons 709 to 718 of the normal RII sequence, or preferably, a two base-pair insertion of GT which occurs in a six base pair repeat sequence GTGTGT at codons 1931–1936 of the normal RII sequence. In a particular embodiment, this heterologous polynucleotide is an expression vector which expresses an inactive mutant form of RII.

In still another embodiment, this invention provides a therapeutic method for treating a cancer patient, wherein neoplastic cells of the patient express a non-functional mutant form of a growth regulatory gene, wherein the growth regulatory gene encodes a type II receptor which is a member of a family of serine/threonine receptors which bind members of a family of TGFβ-like factors or the wild-type of the growth regulatory gene contains repetitive DNA sequence motifs in the coding region, the method comprising administering to the patient an immunogenic amount of an immunogenic composition comprising a non-functional mutant form of the growth regulatory gene product or an expression vector encoding the same non-functional mutant form of the growth regulatory gene as the neoplastic cells of the patient. In a particular embodiment, this invention provides a therapeutic method for treating a colon cancer patient whose tumor expresses a mutant form of RII by administering to the patient an immunogenic amount of an expression vector encoding mutant TGFβ receptor RII which is the same mutant form of RII as expressed by the patient's tumor cells.

In still another embodiment, this invention provides a mutant protein of human TGFβ receptor RII substantially free of other human proteins, the mutant RII protein having a sequence encoded by RII cDNA altered by a mutation, the mutation being either deletion or insertion of one or two A base pairs in a ten base-pair poly A sequence at codons 709 to 718 of the normal RII sequence, or preferably, a two base pair insertion of GT which occurs in a six base pair repeat sequence GTGTGT at codons 1931–1936 of the normal RII sequence. This invention also provides antibodies specific for the mutant protein.

In yet another embodiment, this invention provides a therapeutic method for treating a colon cancer patient, where the patient's tumor cells express a mutant form of RII, the mutation being a two base pair insertion of GT which occurs in a six base pair repeat sequence GTGTGT at codons 1931–1936 of the normal RII sequence, or deletion or insertion of one or two A base-pairs in a ten base pair poly A sequence at codons 709 to 718 of the normal RII sequence, comprising administering to the patient an immunogenic composition containing a mutant form of RII containing the same RII mutation as the tumor cells of the patient.

In yet another embodiment, this invention provides a therapeutic method for treating a cancer patient, wherein neoplastic cells of the patient express a non-functional mutant form of a growth regulatory gene, wherein the growth regulatory gene encodes a type II receptor which is a member of a family of serine/threonine receptors which bind members of a family of TGFβ-like factors or the wild-type of the growth regulatory gene contains repetitive DNA sequence motifs in the coding region, the method comprising administering to the patient an effective amount of an substance specifically immunoreactive with the non-functional mutant form of the growth regulatory gene expressed by the neoplastic cells of the patient, the substance being preferably antibodies specifically immunoreactive with the growth regulatory gene or specific activated cytotoxic immune cells. In a preferred embodiment, the therapeutic method comprises administering a substance specifically immunoreactive with RII, the type II receptor for TGFβ.

In still another embodiment, this invention provides a therapeutic method for treating a cancer patient, wherein neoplastic cells of the patient express a non-functional mutant form of a growth regulatory gene, wherein the growth regulatory gene encodes a type II receptor which is a member of a family of serine/threonine receptors which bind members of a family of TGFβ-like factors or the wild-type of the growth regulatory gene contains repetitive DNA sequence motifs in the wild-type coding region, the method comprising administering to the patient a gene therapy vector encoding a functional form of the growth regulatory gene expressed by the neoplastic cells of the patient, the gene being operably linked to a promoter, wherein said gene therapy vector is expressed in the patient to produce a functional form of the growth regulatory gene expressed by the neoplastic cells of the patient. In a particular embodiment, this invention provides a therapeutic method for treating a patient having colon cancer of the RER phenotype comprising administering to the patient a gene therapy vector encoding functional TGFβ receptor RII operably linked to a promoter, wherein the gene therapy vector is expressed in the patient to produce functional RII.

In investigations to determine whether inactivation of TGF-β receptors is a mechanism by which human colon cancer cells lose responsiveness to TGF-β, it was discovered that RII receptors were inactivated in a subset of colon cancer cell lines. Surprisingly, RII inactivation was a common characteristic of tumor cells exhibiting microsatellite instability (hereafter referred to as RER+, for "replication errors"). Inactivation of RII, by frameshift mutations in regions of small repeat sequences, appears to be a critical step in tumor progression, rather than a simple correlate of the RER+ phenotype.

BRIEF DESCRIPTION OF THE FIGURES

FIG. 3 illustrates expression of cell surface TGF-β receptors in RER+ and RER− colon cancer cell lines measured by TGF-β binding studies. The VACO group of colon cancer cell lines are indicated by the prefix V. The two panels present results of two independent experiments.

DETAILED DESCRIPTION OF THE INVENTION

Figure 1A:
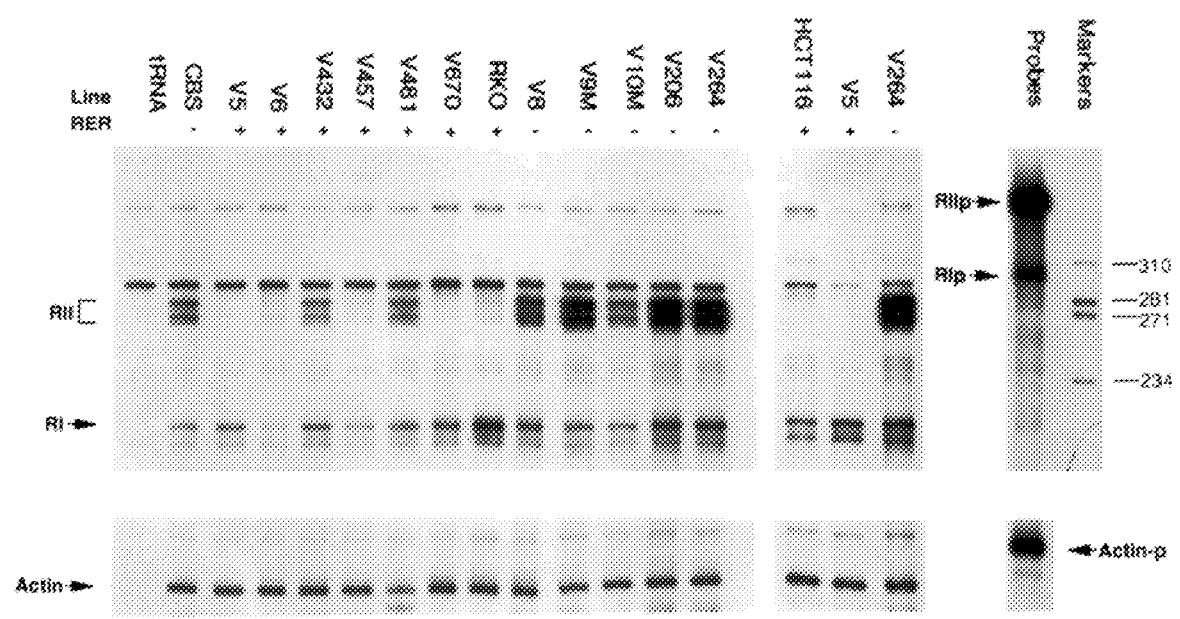
FIG. 1A shows expression of type RI and RII transcripts in RER+ and RER− colon cancer cell lines measured by RNase protection assay.

TGF-β is a natural inhibitor of growth of human epithelial cells. TGF-β is expressed by normal colon epithelium (Avery, A., et al., 1993, Brit. *J. Cancer,* 68:137), by malignant colon epithelium (Avery, A., et al., 1993) and by most colon cancer cell lines (Brattain, et al., 1994, *Curr. Opin. Oncol.,* 6:77). Exogenous addition of TGF-β has been shown to abolish the proliferation of early colon neoplasms studied as cell lines (Markowitz, S., et al., 1994, *J. Clin. Invest.,* 93:1005). In colon and in other cell types studied, inactivation of the TGF-β receptor RII permits escape from TGF-β mediated growth inhibition (Geiser, et al., 1992, *J. Biol. Chem.,* 267:2588; Wrana, J., et al., 1992, *Cell,* 71:1003; Boyd, et al., 1989, *J. Biol. Chem.,* 264:2272; Laiho, et al., 1991, ibid., 266:9108; Laiho, et al., 1990, ibid., 265:18518). The inventors have determined that restoring wild-type RII expression (by gene transfection) suppresses the in vivo tumorigenicity of both receptor-negative breast and colon cancer cell lines.

The inventors have discovered that colon cancer cell lines demonstrating high rates of microsatellite instability (RER$^+$) also, unexpectedly, demonstrate mutations in the type II TGF-β receptor (RII). Eight such examples, due to three different mutations, have been identified. Mutations are within small repeat sequences in the RII gene, are accompanied by absence of cell surface RII receptors, and are associated with mostly low levels of RII transcript. This discovery links DNA repair defects with a pathophysiologic step in colon carcinogenesis, and defines a possible pathway for progression of RER tumors, involving escape from TGF-β mediated growth control by RII mutation.

Previous studies have demonstrated hypermutability in RER$^+$ cell lines, within both DNA microsatellites and within expressed gene sequences (Aaltonen, L., et al., 1993, *Science,* 260:812; Ionov, et al., 1993, *Nature,* 363:558; Thibodeau, et al., 1993, *Science,* 260:816; Kim, et al., 1994, *Am. J. Pathol.,* 145:148; Eshleman, J., et al., 1995, *Oncogene,* 10:33). The type II TGF-β receptor appears to be a common target for mutation in RER$^+$ colon cancers and, as such, links DNA repair defects (see Aaltonen, L., et al., 1993; Ionov, et al., 1993; Thibodeau, et al., 1993; Kim, et al., 1994; Liu, B., et al., 1995, *Nature Genet.,* 9:48; Papadopoulos, N., et al., 1994, *Science,* 263:1625; Bronner, C., et al., 1994, *Nature,* 17:258; Fishel, R., et al., 1993, *Cell,* 75:1027; Leach, F., et al., 1993, ibid., 75:1215; and Nicolaides, N., et al., 1994, *Nature,* 371:75 for DNA repair defects) with a demonstrable pathophysiologic event. Small repeat sequences in the RII gene appear to make it a favorable target for RER$^+$ associated mutator mechanisms. The proliferative advantage of cells with inactivated RII drives tumor progression forward once these cells are generated. This pathway for tumor progression may additionally be operative in those non-colonic human malignancies in which the RER$^+$ phenotype has also been detected, such as endometrial cancer, ovarian cancer, gastric cancer, pancreatic cancer and other malignancies (reviewed in Eshleman, et al., 1995, in Willison, ed., "Current Opinion in Oncology," *Current Science,* Philadelphia, p. 83).

Tumor progression by RII inactivation may additionally be operative in other cancers, such as non-RER colon cancer or breast cancer, in which RII may be inactivated by mechanisms other than these specific RER associated mutations. The diagnostic procedures for detecting inactivation of RII as described herein and the benefits of therapeutic intervention aimed at restoring RII function provided below will be applicable to these other cancers as well. In particular, a substantial subset of human breast cancers lack functional RII, and that lack of functional RII is particularly characteristic of breast cancers which are positive for presence of the estrogen receptor (ER+). RII inactivation in this case may be via mechanisms other than by those mutations found typical of RER+ cancers (e.g. by other types of mutations in either coding region or promoter sequences, or by alternations in RII transcription regulation). The strategies outlined below for cancer detection, diagnosis, prognosis, and treatment of tumors with absent (inactive) RII are applicable to these tumors as well. The same will also be true for those minority of non-RER colon cancers in which RII is inactivated.

RII is one of a group of type II receptors which are members of the family of serine-threonine kinase receptors which bind to the family of ligands sharing structural homology to TGFβ. The TGFβ family of growth factors includes TGF-βs, activins, inhibins; Mullerian inhibitory substance (MIS), and the bone morphogenic proteins (BMPs) as well as closely related members isolated from non-mammalian species such as Drosophila and Xenopus. Because of the roles of these various factors in differentiation, development and inhibition of cellular proliferation, the factors may also be expected to be involved in disruptions of regulatory functions which play a role in determining the cancer genotype and phenotype.

Each member in this family of growth factors carries out its activity by binding to and activating a receptor dimer similar to the TGFβ type II and type I receptors. These constitute the type I and type II serine/threonine kinase receptor subfamilies (Massague, et al., 1994, *Trends in Cell Biology,* 4:173–178). Various type II receptors which have been discovered in this family include Act R-II, Act R-IIB and C14 for activins, activins, and MIS, respectively. Various type I receptors have been designated Act RIB, Act RI (TSK 7L, Alk2, R1), TSR-1 and TβR-1 which bind activins and TGFβs. Mutations of either the type I or the type II receptors in this family would result in a growth regulatory dysfunction similar to that described for the TGF-β type II receptor (RII). Thus monitoring these members of the receptor subfamilies will also prove useful in the diagnosis, prognosis and treatment of cancer.

RII is also one of a group of growth regulatory proteins bearing repetitive DNA sequence elements of 1 to three base pairs in length (reviewed in Ross, et al., in *Trends in Neurosciences,* 1993, vol. 16, pp. 254–261). Instability of these repetitive sequences in nerve or muscle tissues has previously been associated with neurologic diseases. Instability of these sequences homologous to the repetitive DNA sequences in RII, would also be expected to be present in RER cancers, and to be selected for in those instances, in which like RII, such mutations conferred a growth advantage on the tumor.

DEFINITIONS

In describing the present invention, the following terminology is used in accordance with the definitions set out below.

A "double-stranded DNA molecule" refers to the polymeric form of deoxyribonucleotides (adenine, guanine, thymine, or cytosine) in its normal, double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed stand of DNA (i.e., the strand having a sequence homologous to the mRNA).

A DNA sequence "corresponds" to an amino acid sequence if translation of the DNA sequence in accordance with the genetic code yields the amino acid sequence (i.e., the DNA sequence "encodes" the amino acid sequence).

One DNA sequence "corresponds" to another DNA sequence if the two sequences encode the same amino acid sequence.

Two DNA sequences are "substantially similar" when at least about 85% (preferably at least about 90%, and most preferably at least about 95%) of the nucleotides match over the defined length of the DNA sequences. Sequences that are substantially similar can be identified in a Southern hybridization experiment under, for example, stringent conditions as defined for that particular system. Defining appropriate hybridization conditions is within the skill of the art. See e.g., Maniatis et al., infra; DNA Cloning, vols. 1 and II infra; Nucleic Acid Hybridization, infra.

A "heterologous" region or domain of a DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous region is a construct where the coding sequence itself is not found in nature (e.g., a cDNA where the genomic coding sequence contains introns, or synthetic sequences having codons different than the native gene). Allelic variations or naturally occurring mutational events do not give rise to a heterologous region of DNA as defined herein.

A coding sequence is an in-frame sequence of codons that (in view of the genetic code) correspond to or encode a protein or peptide sequence. Two coding sequences correspond to each other if the sequences or their complementary sequences encode the same amino acid sequences. A "coding sequence" in association with appropriate regulatory sequences may be transcribed and translated into a polypeptide in vivo. A polyadenylation signal and transcription termination sequence will usually be located 3' to the coding sequence. A "promoter sequence" is a DNA regulatory region capable of binding RNA polymerase in a cell and initiating transcription of a downstream (3' direction) coding sequence. A coding sequence is "under the control" of the promoter sequence in a cell when RNA polymerase which binds the promoter sequence transcribes the coding sequence into mRNA which is then in turn translated into the protein encoded by the coding sequence.

For purposes of defining the present invention, the promoter sequence is bounded at its 3' terminus by the translation start codon of a coding sequence and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eucaryotic promoters will often, but not always, contain "TATA" boxes and "CAT" boxes. Procaryotic promoters contain Shine-Delgarno sequences in addition to the −10 and −35 consensus sequences.

A cell has been "transformed" by exogenous DNA when such exogenous DNA has been introduced inside the cell wall. Exogenous DNA may or may not be integrated (covalently linked) to chromosomal DNA making up the genome of the cell. In procaryotes and yeast, for example, the exogenous DNA may be maintained on an episomal element such as a plasmid. With respect to eukaryotic cells, a stably transformed cell is one in which the exogenous DNA is inherited by daughter cells through chromosome replication. This stability is demonstrated by the ability of the eukaryotic cell to establish cell lines or clones comprised of a population of daughter cells containing the exogenous DNA.

A "clone" is a population of cells derived from a single cell or common ancestor by mitosis.

A "cell line" is a clone of a primary cell that is capable of stable growth in vitro for many generations.

Vectors are used to introduce a foreign substance, such as DNA, RNA or protein, into an organism. Typical vectors include recombinant viruses (for DNA) and liposomes (for protein). A "DNA vector" is an autonomously replicating DNA molecule, such as plasmid, phage or cosmid, to which another DNA segment may be attached so as to bring about the replication of the attached segment.

An "expression vector" is a DNA vector which contains regulatory sequences which will direct protein synthesis by an appropriate host cell. This usually means a promoter to bind RNA polymerase and initiate transcription of mRNA, as well as ribosome binding sites and initiation signals to direct translation of the mRNA into a polypeptide. Incorporation of a DNA sequence into an expression vector at the proper site and in correct reading frame, followed by transformation of an appropriate host cell by the vector, enables the production of mRNA corresponding to the DNA sequence, and usually of a protein encoded by the DNA sequence.

A composition comprising a selected component A is "substantially free" of another component B when component A makes up at least about 75% by weight of the combined weight of components A and B. Preferably, selected component A comprises at least about 90% by weight of the combined weight, most preferably at least about 99% by weight of the combined weight. In the case of a composition comprising a selected biologically active protein, which is substantially free of contaminating proteins, it is sometimes preferred that the composition having the activity of the protein of interest contain species with only a single molecular weight (i.e., a "homogeneous" composition).

As used herein, a "biological sample" refers to a sample of tissue or fluid isolated from a individual, including but not limited to, for example, plasma, serum, spinal fluid, lymph fluid, the external sections of the skin, respiratory, intestinal, and genitourinary tracts, tears, saliva, milk, blood cells, tumors, organs, and also samples of in vivo cell culture constituents (including but not limited to conditioned medium resulting from the growth of cells in cell culture medium, putatively virally infected cells, recombinant cells, and cell components).

"Human tissue" is an aggregate of human cells which may constitute a solid mass. This term also encompasses a suspension of human cells, such as blood cells, or a human cell line.

The term "antibodies" encompasses whole antibodies made up of four immunoglobulin peptide chains, two heavy chains and two light chains, as well as immunoglobulin fragments. "Immunoglobulin fragments" are protein molecules related to antibodies, which are known to retain the epitopic binding specificity of the original antibody, such as Fab, F(ab)'$_2$, Fv, etc.

General Methods

The practice of the present invention employs, unless otherwise indicated, conventional molecular biology, microbiology, and recombinant DNA techniques within the skill of the art. Such techniques are well known to the skilled worker and are explained fully in the literature. See, e.g., Maniatis, Fritsch & Sambrook, "Molecular Cloning: A Laboratory Manual" (1982); "DNA Cloning: A Practical Approach," Volumes I and II (D. N. Glover, ed., 1985); "Oligonucleotide Synthesis" (M. J. Gait, ed., 1984); "Nucleic Acid Hybridization" (B. D. Hames & S. J. Higgins, eds., 1985); "Transcription and Translation" (B. D. Hames & S. J. Higgins, eds., 1984); "Animal Cell Culture" (R. I. Freshney, ed., 1986); "Immobilized Cells and Enzymes" (IRL Press, 1986); B. Perbal, "A Practical Guide to Molecular Cloning" (1984), and Sambrook, et al., "Molecular Cloning: a Laboratory Manual" (1989).

Detecting RII Inactivation

Inactivation of RII can be monitored by any assay which measures RII, its precursor molecules or its effects. Inactivation can be detected from the absence of RII or a precursor in an assay specific for the presence of RII or by positive detection of a mutant form known to be inactive. The presence of mutant forms of RII can also be detected indirectly, by positive detection in serum from a patient of antibodies specific for mutant RII. Detection of antibodies specific for wild-type RII, demonstrating that self-tolerance of RII has been broken, is another indicator that RII has been altered in a fashion that suggests inactivation.

Detection of RII proteins and their expression, may be on the nucleotide or peptide level. Anti-RII antibodies can be prepared by immunizing mammals with peptides expressed from nucleic acid sequences corresponding to RII as indicated in International Patent Publication WO 93/09228, incorporated herein by reference, using techniques that are well known to those skilled in the art. These antibodies can detect the presence of RII protein by a variety of immunoassay techniques. The nucleotide probe sequences provided herein can be used to detect expression of mRNA corresponding to RII proteins or mutant forms of RII in accordance with any of the standard techniques. Expression may be detected either by in situ hybridization or by extraction and detection of mRNA. Sequences encoding mutant forms of RII may also be detected on the genomic level. The particular procedures for gene probe assays and immunoassays are well-known to those skilled in the art. Peptides having enough of the sequence for TGFβ RII to contain one or more epitopes can be produced from the sequence disclosed in WO 93/09228, and these peptides can be used to detect antibodies specific for wild-type RII molecules. Similar assays can be used to detect inactivation or inactive mutants of the other members of the type II serine/threonine kinase receptor family.

Three assays have been used preferentially for detecting the inactivation of RII. The first assay is an RNase protection assay which detects loss of RII RNA. The second assay is a TGF-β binding assay which detects the absence of functional RII receptor protein. The chemistry of these two assays and their use in model systems are described in Sun, et al., 1994, J. Biol. Chem., 269:26449–26455, incorporated herein by reference, and details of these assays are provided in the Examples below. RII inactivation has also been determined by direct cloning and sequencing of mutant RII receptor from colon cancer cell lines which are not sensitive to exogenous TGF-β. Three mutations in the RII gene are described in detail in the Examples. The findings from all three assays as applied to human colon cancer are also described in the Examples.

Assays for Loss of RII mRNA

RII mRNA transcripts must be present in the cell for synthesis of the RII receptor to occur. Therefore, mutations that result in decreased stability or outright failure to produce RII mRNA will make cells insensitive to TGF-β. Loss of RII mRNA can be detected, for instance, by hybridization of probes with RII sequences to mRNA in situ or by RNase protection. Any effective method for detecting the presence or absence of RII mRNA in a sample of cells from tumor tissue is within the scope of this invention.

The RII Nucleotide Sequence

The DNA sequence encoding RII can be synthesized chemically or isolated by one of several approaches using the sequence information provided in International Patent Publication WO 93/09228 or the sequence provided in Genbank under accession no. M85079 (SEQ ID NO:8, SEQ ID NO:9). The complete sequence may be assembled from overlapping oligonucleotides prepared by standard methods and assembled into a complete coding sequence. See, e.g., Edge (1981) Nature 292:756; Nambair, et al. (1984) Science 223:1299; Jay, et al. (1984) J. Biol. Chem., 259:6311. The isolation methods will rely in part on nucleic acid hybridization using appropriate single stranded or double stranded nucleotide or oligonucleotide probes. Such probes can be constructed synthetically, based on the DNA or amino acid sequences disclosed herein, or isolated from genomic or cDNA clones also described herein. The basic strategies for preparing oligonucleotide probes and DNA libraries, as well as their screening by nucleic acid hybridization, are well known to those of ordinary skill in the art. See, e.g., Sambrook, et al., "Molecular Cloning: a Laboratory Manual" (1989); B. Perbal, "A Practical Guide To Molecular Cloning" (1984). In general, the probes are synthesized chemically, preferably based upon known nucleic acid sequences of RII or its mutants as disclosed herein.

One of skill in the art may find it desirable to prepare probes that are fairly long and/or encompass regions of the amino acid sequence which would have a high degree of redundancy in the corresponding nucleic acid sequences. In other cases, it may be desirable to use two sets of probes simultaneously, each to a different region of the gene. While the exact length of any probe employed is not critical, typical probe sequences are no greater than 1000 nucleotides in length, more typically they are not greater than 500 nucleotides, even more typically they are no greater than 250 nucleotides; they may be no greater than 100 nucleotides, and also may be no greater than 75 nucleotides in length. Generally it is recognized in the art that probes from about 14 to about 20 base pairs are usually effective. Longer probe sequences may be necessary to encompass unique polynucleotide regions with differences sufficient to allow related target sequences to be distinguished. For this reason, probes are preferably from about 10 to about 100 nucleotides in length and more preferably from about 20 to about 50 nucleotides.

Nucleotide Probe Assays for Expression

The nucleic acid probes described above may be used to detect mRNA transcripts in cells that express RII. The probe can be either single or double stranded DNA or RNA. The size of a probe can vary from less than approximately 20 nucleotides to hundreds of nucleotides. The most desirable nucleotide probes do not detect nucleotide sequences unrelated to their intended target, do not show significant homology with unrelated nucleotide sequences, and do not contain complementary sequences such that they would self-hybridize or fold upon themselves. The guanine and cytosine content of desirable probes is not so high as to promote non-specific hybridization with unrelated sequences rich in guanine and cytosine. Finally, the melting temperature and free energy of binding are generally favorably suited to the detection technique for which they are intended. The probe may be radio-labeled, labeled with a fluorescent material, a biotinylated nucleotide, or the like. Procedures for the preparation and labeling of nucleotide probes are well known in the art.

In situ hybridization of nucleotide probes to tissue sections is performed using standard methods, as described by, e.g., Baldino, et al., *Methods in Enzymol.*, 1989, vol. 168, p. 761–77; Emson, et al., *Methods in Enzymol.*, 1989, vol. 168, p. 753–61; Harper, et al., *Methods in Enzymol.*, 1987, vol. 151, p. 539–51; Angerer, et al., *Methods in Enzymol.*, 1987, vol. 152, p. 649–61; Wilcox, et al., *Methods in Enzymol.*, 1986, vol. 124, p. 510–33, incorporated herein by reference, using nucleotide probes described above. One preferred method for detecting mRNA associated with expression of RII or RII mutants is in situ hybridization to tissue sections taken from tumors. Detection of hybridization by a probe having a nucleotide sequence corresponding to RII in the cells indicates expression by that cell of mRNA corresponding to RII. Tissue sections are prepared as for immunohistochemistry.

Alternatively, extracts of RNA from tissue samples can be analyzed for the presence of sequences encoding the proteins of this invention. The diagnostic test employing a nucleotide probe will employ a biological sample from an individual. Nucleic acids are recovered from the sample employing standard techniques well known to those skilled in the art. The nucleic acid then is incubated with the probe and hybridization is thereafter detected. The presence of a nucleic acid whose sequence corresponds to that of the probe is preferably detected by Northern blot, or slot/dot blot. Using Northern blotting or dot hybridization, purified RNA samples of known concentration and integrity can be hybridized with labeled RII probes. For each sample, the signal which is obtained can be compared radiometrically to the signal obtained when the same sample is hybridized to a labelled probe for a constitutively expressed gene whose expression does not vary from cell to cell or sample to sample. Comparison of the ratios between different samples permits estimation of the differences in RII expression levels.

Alternatively, a nucleic acid whose sequence corresponds to the sequence of RII may be detected in the RNA extract of tumor tissue by nucleic acid amplification, using primers based on the nucleic acid sequence of RII (see, e.g., methods reviewed in Van Brunt, BioTechnology, 8:291–294, 1990). Similar primers can be used to amplify genomic DNA sequences encoding RII or RII mutants. The preferred method of amplification uses the polymerase chain reaction (PCR). Primers can be constructed corresponding to unique portions of the nucleic acid sequence of RII, determined as described above for nucleic acid probes. Using these primers, RNA or DNA in a nucleic acid extract of tumor tissue will be amplified by PCR only if it contains the unique RII sequences.

Alternatively, the level of RII mRNA expression can be estimated by quantitative polymerase chain reaction. Using primers whose sequences correspond to the RII nucleotide sequence, cDNA can be synthesized initially using reverse transcriptase, then the resultant cDNA amplified according to the polymerase chain reaction. The reaction is run under conditions and terminated so as to produce amounts of amplified products in proportion to the amount of mRNA originally present in the sample. The amount of product can be quantitated by ethidium fluorescence in comparison to known standards following electrophoresis, or by dot hybridization with labeled probes. Expression of constitutively expressed genes can be measured as a control, permitting standardized comparison of results, such as with the previously described hybridization reactions. Treatment of samples with ribonuclease A or other RNAses in control samples prior to amplification verifies that the signal is derived solely from RNA.

RNase Protection Assay For Detection Of RII Transcript

A preferred method for detecting loss of mRNA is based on RNase protection. Details of this assay have been published in Sun, et al. Briefly the RNase protection assay measures the amount of RII mRNA in a sample by measuring the amount of RNA which binds to a radioactive antisense RII RNA probe. The radioactive antisense RII RNA probe is produced in a test tube, for example from a plasmid which carries 264 bp for RII cDNA (NarI-PstI) cloned downstream of a T3 RNA polymerase site from which the RNA can be transcribed. Usually, a control human probe such as γ-actin RNA is also prepared from a similar plasmid. The probes are hybridized overnight at room temperature in a guanidine buffer with RNA extracted from tumor cells. The next morning probe RNA which is not protected by binding to authentic RII transcript is destroyed by digestion with RNase A+T1. Protected probe RNA is separated from the reaction by electrophoresis on a urea-acrylamide gel and visualized by autoradiography.

RNA probes may also be designed for detection of RNA transcripts from the type I TGF-β receptor gene (RI) by RNase Protection Assay based on the RI sequence (see, e.g., Genbank Accession No. L11695). A suitable RI probe corresponds to the 164 bp 3' fragment produced by HinfI digestion of that portion of the RI sequence bounded by PCR sense primer 5' GACCAGTGTGCTTCGTCTGC-3' SEQ ID No:1 and antisense primer 5'GCTGGCTTTCCTTGGGTACC-3 SEQ ID No:2.

Absence of the Wild-Type RII Protein

It has been shown that functional RII receptor must be present in the cell membrane and at the cell surface to mediate TGF-β effects, and therefore inactivation of the TGF-β growth suppression can be monitored by any method for detecting the absence of functional RII on the cell surface. The presence of RII can be measured by immunoassay, using antibodies specific for RII, such as those described in International Patent Publication WO 93/09228, incorporated herein by reference. Lack of antibody binding would indicate the absence of functional RII molecules. Inactive RII receptors may also be detected by using anti-RII antibodies to detect either aberrant cellular location (e.g., on immunohistochemistry) or by virtue of aberrant molecular size (e.g., on Western Blot assays). Alternatively, antibodies specific for the inactive mutant forms of RII described below may be used to detect the presence of inactive RII directly. Antibodies to the inactive mutants may be prepared by standard methods including expression of the mutant protein in a recombinant system from the nucleic acid sequence disclosed herein and immunization of a mammal using the expressed protein.

The absence of functional RII also results in absence of functional RI cell surface receptors (Wrana, et al., (1992)

Cell, 71:1003; Sun, et al., (1994) J. Biol. Chem., 629:26449). Accordingly, absence of functional RI may serve as a useful surrogate for absence of functional RII. Hence, detection of absent functional RI, by antibody reagents specific for RI, such as antibody V-22 (catalogue # sc-398, Santa Cruz Biotechnology, Inc., Santa Cruz, Calif.), would represent another antibody-based approach for identifying cells with inactive RII.

Antibody Production

Antibodies which are specifically reactive with the mutant RII proteins of this invention may be obtained in a number of ways which will be readily apparent to those skilled in the art. The mutant protein can be produced in a recombinant system using the mutant nucleotide sequence disclosed below (see, e.g., Sambrook et al.). The recombinant protein can be injected into an animal as an immunogen to elicit polyclonal antibody production. The resultant polyclonal antisera may be used directly or may be purified by, for example, affinity absorption using recombinantly produced RII or RII mutants coupled to an insoluble support.

In another alternative, monoclonal antibodies specifically immunoreactive with the protein may be prepared according to well known methods (See, e.g., Kohler and Milstein, 1976, Eur. J. Immunol., 6:611), using the peptide of this invention as an immunogen, using it for selection or using it for both functions. These and other methods for preparing antibodies that are specifically immunoreactive with the recombinant protein of this invention are easily within the skill of the ordinary worker in the art. Preferably antibodies specific for mutant RII will not react with normal (wild type) RII. Similar methods can be used to produce antibodies specifically immunoreactive with wild-type RI or RII, as will be apparent to the skilled worker.

Immunoassays

The antibodies of the present invention can be used to detect RI, RII or RII mutants in histological sections. One can detect antibody binding to tissue sections by any detection means known in the art for example, a radiolabel or a stain. A particularly useful stain employs peroxidase, hydrogen peroxide and a chromogenic substance such as aminoethyl carbazole. For example, the peroxidase (a well known enzyme available from many sources) can be coupled to an anti-RII antibody or merely complexed via one or more antibodies to an antibody which specifically binds a protein which is cross-reactive with RII. Such techniques are well known in the art. Other chromogenic substances and enzymes may also be used. Fluorescence labelling or radiolabeling of antibodies may also be used to detect antibody binding to sections. Labeled antibodies may be anti-RII or second antibodies immunoreactive with anti-RII antibodies. Again, such techniques are well known, and equivalent labelling schemes for the other antigens will be apparent to the skilled worker.

The precise technique by which a protein cross-reactive with the RI, RII or mutant RII gene product is detected in patients is not critical to the invention. Biochemical or immunological techniques can be used which do not employ immunohistochemistry. Solution assay methods, including colorimetric, chemiluminescent or fluorescent immunoassays such as ELISA, sandwich and competitive immunoassays, immuno-diffusion, radio immunoassay, immunoelectrophoresis, Western blot and other techniques, may be used to detect and quantitate proteins cross-reactive with RI, RII or RII mutants in a patient by preparing an extract of a tissue sample from the patient and assaying the extract.

A protein cross-reactive with the RI, RII or mutant RII gene product can be quantitated in a biological fluid, such as serum, plasma, effusions, ascites, urine, stool, cerebrospinal fluid, semen, breast aspirates and fluids of ovarian origin, using any protein detection means known in the art. Preferred methods employ immunological detection means. These include: radioimmunoassay, enzyme linked immunoadsorbent assay, complement fixation, nephelometric assay, immunodiffusion or immunoelectrophoretic assay and the like. Plasma should be anticoagulated before use, as is known in the art. Cellular elements and lipid may be removed from fluids, e.g., by centrifugation. For dilute fluids, such as urine, protein may be concentrated, e.g., by ultra-filtration or salting-out.

Alternatively, the presence of mutant RII in a patient may be detected by immunoassays which detect production of an antibody response in the patient aimed against either the RII mutation or, due to breaking of immune tolerance, against other epitopes on the native RII protein. The provocation in a patient of a serologic antibody response to oncogenic mutation in a protein has been previously demonstrated in patients whose tumors harbor oncogenic mutations in the p53 protein (reviewed in Harris, et al., 1993, N. Eng. J. Med., 329:1318–1327). As frameshift mutations located within the ten base-pair poly A sequence at codons 709–718 would be predicted to encode RH proteins truncated prior to their membrane spanning domain, it is expected such RII mutant proteins would be secreted directly into the blood, and would accordingly provoke a much more vigorous immune response than the mutations in the intracellular p53 protein discussed by Harris, et al. Such an immune response could provoke production of antibodies in the patient against epitopes in the mutant RII sequence or, as has been seen in some patients bearing tumors harboring p53 mutations, could result in breaking immune tolerance and so provoking an antibody response to epitopes on the native RII protein. Detection of a patient's serologic response to RII, using standard methods such as radioimmunoassay, or enzyme linked immunosorbant assay (ELISA), or other similar assays, is a routine matter for one skilled in the art.

TGF-β Binding Assay

A preferred method of detecting the presence of functional RII is by TGF-β binding assay in which labelled TGF-β binds to RII followed by cross-linking and measurement of the amount of label linked to RII protein. Details of this assay have been published in Sun, et al., incorporated herein by reference. Briefly, cell surface receptors may be detected by cross-linking in situ to $^{125}$I labelled TGF-β followed by separation on SDS-PAGE and visualization by autoradiography as described in Example 3 below.

Mutations

Cell lines identified as having inactivated RII have been used for the purpose of identifying new RII mutations for subsequent commercial use in cancer detection, diagnosis, prognosis, or therapy. Such cell lines include Hct116, RKO, C, VACO457, VACO670, VACO432, VACO444, VACO5, VACO6, VACO8, VACO703, and VACO481. Each of these colon cancer cell lines bears an inactivated mutant RII gene. The specific mutation in RII in each of these cell lines provides for specific tests to identify that mutant RII product. The tests may be based on either anti-mutant antibody or mutant DNA or RNA probes, or detection of host immune (antibody) response to RII or to RII mutants. Such tests, aimed at detecting the RII mutations which are most common in human cancers, have direct application to cancer detection, diagnosis and prognosis. Moreover, drugs aimed at the most common mutations may be screened for potential use in cancer therapeutics.

The RII mutation identified in the VACO481 tumor may be useful in the development of a commercial test for RII mutation. We have identified the first RII mutation demonstrated to be present in a spontaneous human colon cancer. This mutation eliminates the last 33 normal amino acids in the RII protein and substitutes 29 new ones. The predicted carboxyl-terminal amino acid sequence of the VACO481 RII mutant starting at the last amino acid in common with the wild-type (Val 534) is: VWQNASVSWSIWTGSRGGAAR-RRRFLKTAP SEQ ID NO:5. The corresponding wild-type carboxyl terminal sequence is: VAERFSELEHLDRLSGRSCSEEKIPEDGSLNTTK SEQ ID NO:6.

Additional mutants detected include those found in VACO457 and in RKO. In the VACO457 mutant the wild-type ten base-pair poly-adenine repeat (nucleotides 709–718) is truncated by one base. This encodes a truncated polypeptide of 161 amino acids (compared to 567 amino acids in wild-type) of which the last 34 amino-acids (SLVRLSSCVPVALMSAMTTSSSQKNITPAILTCC) SEQ ID NO:3 are altered from the wild-type, which starting at Lys 128 reads as (KPGETFFMCSCSSDECNDNIIFSEEYN TSNPDLL) SEQ ID NO:4. Similarly, in the RKO mutant the wild-type ten base pair poly-adenine repeat (nucleotides 709–718) is truncated by two bases. This encodes a truncated polypeptide of 129 amino acids in which the last two (AW) are altered from the corresponding wild-type amino acids (KP, starting at Lys 128).

An additional mutation detected is that found in VACO5 and VACO6 in which the wild-type ten base pair poly-adenine repeat (nucleotides 709–718) are expanded by one base. This encodes a truncated polypeptide of 130 amino acids in which the last two (AW) are altered from the corresponding wild-type amino acids (PG, starting at proline 129). A fourth truncated mutant, resulting from two additional base-pairs in the poly-adenine repeat, has the same 34-amino acid C-terminal sequence that is found in VACO457, differing only in that the altered amino acid sequence starts later, by replacement of proline 129 in the wild-type sequence with serine, etc. Similar truncation mutants will occur as a result of further additions or deletions from the ten base-pair poly-adenine repeat sequence.

Another RII mutation is a point mutation of G to A at nucleotide 1899 of the GenBank sequence for RII, resulting in substitution of Asn for Asp 522, which occurs in VACO8, a non-RER colon cancer cell line of mutator phenotype with inactive RII. This point mutation is the first example, in a human tumor, of a point mutation in RII associated with the properties of loss of receptor/ligand binding, loss of the ability of TGFβ to suppress cell growth, and continued presence of RII mRNA transcripts. This point mutation is thus the first example of point mutations in human tumors which inactivate RII and which protein con ligand binding, or receptor protein conformation, receptor protein processing, or receptor protein stability. This class of mutations will be found to occur in tumors which like VACO8 may be identified as being non-RER, and which like VACO8 may be identified by elevated gene mutation rates, and which additionally will be identified by the property of loss of receptor ligand binding, loss of the ability of TGFβ to suppress cell growth, in combination with the continued presence of RII mRNA transcripts. The assays provided herein for these properties of mutant RII receptors can be utilized in conjunction with standard recombinant DNA methods to identify and clone DNA encoding these mutant receptors for use in diagnosis of cancer as described herein.

The RII mutations disclosed above may be expected to be common mutations in many human tumors, and assays for the mutations therefore have use for cancer detection, diagnosis, or possibly prognosis. Such assays include immunoassays using antibodies against the mutant polypeptide, or PCR using primers which amplify the mutant region of the RII gene, or using other DNA or RNA probes to detect the mutant allele. Examples of standard DNA based techniques for detecting mutant gene sequences include: PCR and direct sequencing (see, e.g., McPherson, et al., (1992) *The Practical Approach Series*, Oxford University Press; Sambrook, et al., (1989) *Molecular Cloning: A Laboratory Manual*, Cold Spring Harbor Laboratory Press, Cold Spring Harbor, New York; and Mullis, et al., (1987) *Methods in Enzymology*, 155:335); PCR and allele specific hybridization (see, e.g., Kumar, et al., (1990) *Oncogene*, 5:1271–1277; Kumar, et al., (1990) *Science*, 248:1101–1104; van Mansfeld, et al., (1992) *PCR Meth. Appl*, 1:211–216; Sukumar, et al., (1991) *Mol. Carcinogen*, 4:362–368; and Sukumar, et al., (1990) *Proc. Natl. Acad. Sci., USA,* 87:718–722); the technique of single stranded conformational polymorphisms (SSCP, see, e.g., Iwahana, et al., (1992) *Biotech.*, 12:64–66 and Orita, et al., (1989) *Genomics*, 5:874–879); the mismatch amplification mutation assay (MAMA, see, e.g., Cha, et al., (1992) *PCR Meth. Appl.*, 2:14–20 and Sommer, et al., (1992) *Biotech.*, 12:82–87); and heteroduplex analysis using denaturing gradient gel electrophoresis (DGGE, see, e.g., Fukuda, et al., (1993) *Mol Carcinogen*, 7:257–262; Ruano, et al., (1992) *PCR Meth. Appl*, 2:112–116; and Soto, et al., (1992) *PCR Meth. Appl*, 2:96–98). These assays may be used to detect mutant RII DNA in extracts of tumor tissue or normal tissue, or in biological fluids including stool.

While preferred assays for detection of RII inactivation are described in detail above, other methods of detection will be apparent to the skilled worker, and use of these other methods to detect RII inactivation are also within the scope of this invention for the diagnostic and prognostic uses described below.

Similar assays may be used to detect inactivation or absence of the type I and type II receptors for other members of the family of TGFβ-like factors. Somatic mutation of type II receptors for other TGFβ-like factors will release cells from control of proliferation which is mediated through the particular factor/receptor system, resulting in uncontrolled growth (transformation) of the cells containing the mutation. Such mutations can be characterized as described herein, and once the mutation is characterized, assays for the mutation can be designed using the principles described herein.

Mutants of these receptors can be easily identified in transformed cell lines having reduced or no expression of receptor activity (as determined, for example, by measuring mRNA encoding the receptor, antibody specific for the receptor, binding of the factor to the cells or measurement of bioactivity stimulated by the factor). As described for type II receptor for TGFβ, the receptor can be cloned from a cDNA or genomic DNA library prepared from the transformed cell line using nucleic acid probes or primers derived from the wild-type receptor sequence to select clones from the library. Confirmation that the clones contain DNA encoding mutant receptors can be accomplished by, for example, observing differences in sequence or in the length of the mRNA or the encoded protein. Once clones that encode and/or express the mutant form of the receptor have been isolated, detection of the mutant form of the receptor in patient samples can be readily accomplished by assays analogous to those described for the TGFβ RII receptor.

Similar assays may be used to detect inactivation or absence of other growth regulatory genes which share with RII presence of repetitive DNA sequence elements in their coding region, which we have demonstrated can be targeted for mutation in RER cancers, and whose mutation, would be selected for when, like RII, it confers a growth advantage on the cancer. Identification of such candidate genes can be done by computer searches of gene databases such as GenBank. Examples of such candidate genes found by computer searches include those itemized in Ross, et al., in *Trends in Neurosciences,* 1993, vol. 16, pp. 254–261, for example, the cyclin D gene, the alpha2 adrenergic receptor, and transforming growth factor-β itself.

Use of RII inactivation assay for diagnosis and prognosis

The type II receptor for TGF-β, RII, is a colon cancer suppressor gene which is inactivated in 25% of colon cancers. This indicates important medical uses for assays detecting RII inactivation (defined as above). These uses include predicting a patient's chance of cure or relapse after surgery, radiation, or chemotherapy for colon cancer or other cancers. The present invention is intended to include such use of all assays for detecting RII inactivation, including assays of RII gene mutation, loss of RII messenger RNA, absence of RII receptor protein, and absence of functional RII receptor protein (e.g., presence of mutant RII).

Any test for detection of RII inactivation, by RII loss or RII mutation, may be used in cancer diagnostics, cancer detection, or cancer prognosis, or for use in research laboratories for colon or other cancers such as endometrial cancer, ovarian cancer, gastric cancer, pancreatic cancer and other malignancies. Detection of RII inactivation may be used as an alternate assay for identifying colon or other cancers with unstable microsatellite DNAs (e.g., RER colon cancers, mutator type colon cancers). Any RII mutations in human cancers may be used for the purpose of designing tests for cancer diagnosis, prognosis, or for designing cancer therapy. RII mutations for use in cancer detection, diagnosis, prognosis, or therapy include the mutations in cell lines Hct116, RKO, C, VACO457, VACO670, VACO432, VACO444, VACO5, VACO6, VACO8, VACO703 and VACO481.

In accordance with this invention, it is possible to devise assays for RH inactivation which will work easily on clinical samples of colon or other cancers. Two current assays for detecting RII inactivation (loss of binding of TGF-β to RH or loss of RII transcript) work better in tumor cell lines that in tumor tissue. Assays which will work better in tumors include an anti-RII antibody for use in an immunohistochemical assay, or an assay for RII mutations, such as an in vitro transcription and translation assay, in situ hybridization or RT-PCR assays for detection of RII message or an assay detecting mutant RII genomic sequences, usually after PCR amplification. Alternatively, the presence of mutant RII in a patient may be detected by immunoassays which detect, in the patient, production of an antibody response aimed against either the RII mutation or, due to breaking of immune tolerance, against other epitopes on the native RII protein.

Detection of RER tumor subtype

The RER assay identifies colon cancers with unstable DNA (or Replication ERrors). These types of colon cancers are typical of a common variety of inherited colon cancers. They also present in about 15% of seemingly sporadic colon cancers. It is unknown whether seemingly sporadic RER cancers are truly sporadic or represent inherited colon cancers with a delayed age of onset. The RER assay is a cumbersome one, requiring relatively pure tumor DNA.

Detection of RII inactivation may be used as an alternate assay to identify colon cancers with unstable microsatellite DNAs (RER colon cancers, mutator type colon cancers). Almost all colon cancers of the RER subclass bear an inactivated RII gene. Thus an assay for RII inactivation may functionally replace the current assay for identifying RER colon cancer. This invention contemplates the use of the assays for RII inactivation discussed above (for example, using anti-RII antibodies or in situ hybridization to detect absent RII transcript or detection of mutant RII genomic sequences) as a simple replacement for the RER assay, or to screen tumors to identify those worth doing a confirmatory RER assay on.

While they have been described in conjunction with characterization of the RER subclass of colon cancer, the assays described herein are also useful for identifying other tumor types with unstable microsatellite DNAs, including those of endometrial cancer, ovarian cancer, gastric cancer, and pancreatic cancer.

Cancer Diagnosis

Use of RII inactivation as a molecular marker for colon cancer is a novel idea. Park, et al., 1994, (*Proc. Natl. Acad. Sci. USA.,* 91:8772–8776) reported that RII was inactive in small number of gastric cancer cell lines, but they did not characterize RII mutants, nor did they make the connection that cancers of the RER subclass generally have RII inactivation. Further clinical research on the tumors identified according to this invention will further elaborate how the clinical behavior of colon cancers with inactive RII compares with tumors in which RII is normal. The ultimate clinical use of tests for presence or absence of RII will be in a manner analogous to the current clinical use of assays for presence or absence of estrogen receptors as a guide to therapy in breast cancer patients.

The RII gene appears to be a favorable target for mutations (particularly somatic mutations), and therefore the appearance of mutations in the RII gene may be expected to be an early indication of neoplastic progression. Thus, assays for detecting RII mutations in body tissues or fluids may be used for early detection of cancer or premalignant lesions by detection of cellular changes (RII mutations) before neoplastic changes are observable on the tissue level. These assays may also be used to detect DNA instability in individuals predisposed to cancer development who may be generating multiple premalignant clones bearing RII mutations.

Any test for detection of RII inactivation, by RII inactivation, by RII loss or RII mutation, may be used for the purpose of diagnosis of colon or other cancers. This includes assays of RII gene mutation, loss of RII messenger RNA, absence of RII receptor protein, and absence of function RII receptor protein. Absence of RII or presence of mutant RII protein may be detected in biopsy material by staining with antibodies. Absence of RII transcript may be detected in biopsy material by RNA in situ hybridization techniques. Either assay will facilitate diagnosis of cancer. These assays may be automated by image analyzer. Similarly, mutant RII protein or genes may be detected in body fluids or excreta using PCR techniques, using antibodies directed against the mutations, or using DNA or RNA probes designed to detect the mutations. Presence in a patient of mutant RII protein may also be determined by detection in the patient of an induced antibody response either to the mutant RII protein, or, due breaking of immune tolerance, against other epitopes on the native RII protein. These assays allow early detection of cancers such as colon cancer, in which mutant receptors are present.

The same classes of tests which diagnose cancer by detecting RII inactivation will also be of use for diagnosis of cancer in which genes homologous to RII are inactivated. Such genes will include those encoding type II growth factor receptor subunits belonging to receptors which are members of the family of serine-threonine kinase receptors which bind to the family of ligands sharing structural homology to TGFβ. Such genes will also include those growth regulatory genes which share with RII the property of having in their coding region repetitive DNA sequence motifs.

Prognostic Assay

Detection of RII inactivation is particularly valuable for predicting a patient's chance of cure or relapse after surgery, radiation, or chemotherapy for colon cancer or other cancers. Colon cancers with inactivation of the RII hormone receptor constitute a unique genetic subset of colon cancers which share a specific defect in growth regulation. Assays which identify tumors as having inactivated RII will have prognostic value in predicting the likelihood of the tumors being cured by surgery, by chemotherapy, or by radiation. (This situation is analogous to the situation in breast cancer in which a subset of cancers have loss of the estrogen receptors, this subset having a unique biology leading to lower likelihood of cure by surgery and lack of response to hormonal drugs).

Loss of RII will have prognostic value as shown by our observation that most colon cancers testing positive on the RER molecular assay for unstable DNA also show inactivation of RII. It has already been suggested elsewhere that RER+ colon cancers are more likely to be cured by surgery than are non-RER colon cancers (Thibodeau, et al., *Science,* 206:816 (1993); Lothe, et al., *Cancer Res.,* 52:5849 (1993)). Assays for RII inactivation are easier than the RER assay, and are at least as predictive of tumor outcome.

Any of the inactivating RII mutations discovered in human cancers may be used for the purpose of designing tests for cancer diagnosis and/or prognosis, or for designing cancer therapy. We have established the general principle that human cancers bear RII mutations and that these mutations can be exploited (as outlined above) for use in cancer detection, prognostication, and for design of cancer therapeutic agents targeted at the RII molecule.

This invention also provides specific RNase protection assays for detection of expression or loss of expression of RII and RI ( the type I receptor) for cancer diagnosis, cancer detection, or cancer prognosis, or for use in research laboratories. Specific details of an RNase protection assay for detecting inactivation of RII are detailed above and in the Examples below. RNA probes based on the respective sequences disclosed above may be used in RNase protection assays for detecting inactivation of the other signalling components in the TGF-β growth control pathway, such as RI (the type I TGF-β receptor). These RNase protection assays lend themselves to straightforward incorporation into commercial test kits for use in detecting inactivation of any of these components of the TGF-β pathway. This invention contemplates use of these assays for cancer detection, diagnosis, prognosis and research.

Therapeutic Intervention by RII Replacement

RII gene therapy is contemplated for cancer treatment, including genetic manipulations for introducing a normal RII gene into a cancer cell. Any tumor in which mutation of a receptor for a member of the family of TGF-β-like factors results in unresponsiveness to the respective factor is a candidate for gene therapy to provide the tumor cells with functional receptors, thereby reestablishing control of cellular proliferation. A preferred candidate, TGF-β type II receptor (RII) is a colon cancer suppressor gene which is inactivated in perhaps 25% of colon cancers, and gene therapy to restore functional RII expression in these colon cancers will benefit cancer patients. One important theoretical advantage of RII gene therapy is that it would not be expected to be toxic to normal cells which already express RII.

Gene therapy vectors for use in the method of this invention include retroviral or episomal vectors expressing RII (see, e.g., Axel, et al., U.S. Pat. No. 4,399,216, and Pastan, et al., U.S. Pat. No. 5,166,059, both incorporated herein by reference). Delivery systems as contemplated herein include both viral and liposomal delivery systems (see, e.g., Davis, et al., U.S. Pat. No. 4,920,209, incorporated herein by reference). An RII gene expression vector has been developed, and we have shown it can knock out the ability of a breast cancer cell line to form tumors in mice (See, Sun, et al, 1994). Similar experiments have demonstrated that transfection with an RII gene expression vector can knock out the tumor forming ability of a colon cancer cell line.

We have demonstrated that, in colon cells with intact TGF-β receptors, exposure to TGF-β will induce cell death (apotosis). Thus, therapeutic effects of restoring an active RII in colon cancer cells will include restoring normal cell death pathways. RII gene therapy is thus useful in combination with and to sensitize cells to conventional cytotoxic radiation or chemotherapy.

Another therapeutic use of the RII mutations described herein is their use as targets for tumor immunotherapy. The RII mutants sequences encode tumor specific antigens which may be displayed on the cell surface as mutant receptors or as peptides associated with HLA antigens. As such, they can be employed as targets for tumor immunotherapy. Such approaches include targeting these mutants with specific monoclonal antibodies (either naked or conjugated to tumoricidal agents) or with specific activated cytotoxic immune cells. Such antibodies or immune cells may be generated as reagents outside the body, or may be generated inside the body by vaccines which target these mutations. Immunogenic compositions according to this invention for use in active immunotherapy include recombinant mutant RII protein prepared as described above and expression vectors (particularly recombinant viral vectors) which express mutant RII protein. Such expression vectors can be prepared as described in Baschang, et al., U.S. Pat. No. 4,446,128, incorporated herein by reference, or Axel, et al., Pastan, et al., or Davis, et al., using the mutant RII sequences disclosed herein. Of note, the use of auto-antibodies directed against RII epitopes for cancer diagnosis does not preclude the use of immunotherapy directed against RII epitopes for cancer treatment. This reflects that the clinical effectiveness of immunotherapy for cancer treatment may require the conjugation of the antibodies with tumoricidal agents, or the generation of a cell mediated, rather than a humeral, immune response.

EXAMPLES

In order to facilitate a more complete understanding of the invention, a number of Examples are provided below. However, the scope of the invention is not limited to specific embodiments disclosed in these Examples, which are for purposes of illustration only.

Example 1

Disappearance of RII in RER+ cell lines

Expression of RI and RII transcripts was examined in 38 human colon tumor cell lines using a ribonuclease (RNase) protection assay as described above (see also Sun, et al., 1994). Total RNA (40 μg) from each sample was hybridized overnight in a single reaction to probes for RI, RII and human γ-actin. FIG. 1A shows the autoradiogram of a 7M urea-6% acrylamide gel displaying the reaction products. The RII probe (RIIp) protects a tight doublet of approximately 274 bp, and the RI probe (RIp) protects a 222 bp fragment. The control γ-actin probe (Actin-p) protected a 126 bp fragment. The colon cancer cell lines are indicated above the lanes, with the VACO group of cell lines indicated by the prefix V. A control reaction displays the protection pattern generated by yeast tRNA. The two panels present results from two independent experiments.

Figures 1, 1B:
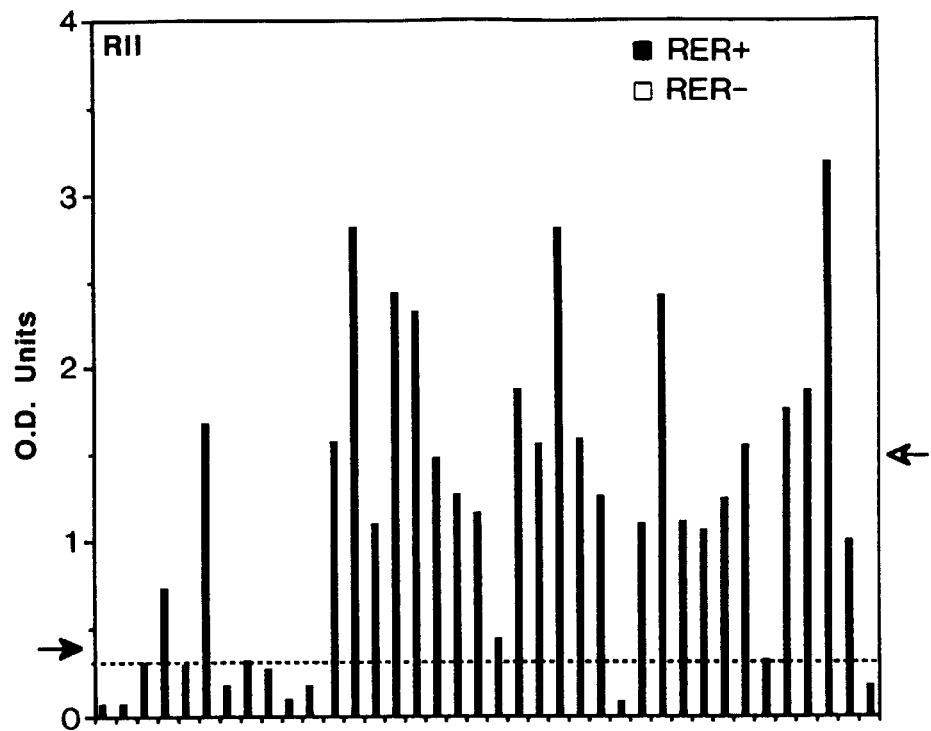
FIG. 1B shows laser densitometric quantitation of RII and RI transcript expression in 38 colon cancer cell lines.

RNase protection patterns (as shown in FIG. 1A) were quantitated by laser densitometry. Variations in sample loading were corrected by normalizing samples for their relative expression of human γ-actin. The relative transcript expression in arbitrary O.D. units is shown in FIG. 1B for 11 RER$^+$ and 27 RER$^-$ cell lines. Arrows show mean level of receptor expression of RER$^+$ (filled arrow) and RER$^-$ cells (open arrow). The broken line indicates the limit at which the naked eye detects a protected transcript at maximally sensitive exposures.

RI transcripts were detected in all samples, whereas RII transcripts were undetectable or present at markedly reduced levels in 12 (32%) of the samples (FIGS. 1A and 1B). These cell lines were independently assayed for RER phenotype. The RER status of these lines was determined as described in Liu, B., et al., 1995, Nature Genet., 9:48. RER+ colon cancers studied were: RKO, HCT116, C, VACO432, VACO444, VACO457, VACO481, VACO5, VACO6, VACO670, and VACO703. (Eshleman, J., et al., 1995, Oncogene, 10:33; Liu, B., et al., 1995, Nature Genet., 9:48) Nine of the 11 RER$^+$, but only 3 of the 27 RER$^-$ lines, showed reduced RII expression (FIG. 1B). This correlation was highly significant (P<0.001 by chi-squared test). Southern (DNA) blot analysis indicated that loss of the RII transcript in the RER$^+$ cells was unlikely to be due to deletions or rearrangements of the RII gene.

Example 2
Disappearance of RII in RER+ tumor xenografts

To show that RII inactivation in the RER$^+$ cells was not simply a trait selected for during cell culture, RII expression was examined in tumor xenografts that had been derived from 30 human colon cancers by implantation into athymic mice. Human colon cancer tissue (5 mm$^2$), obtained at surgical resection, was subcutaneously implanted into the forelimbs of athymic mice. Xenografts were removed when they were 1000 mm$^3$ in size.

Figures 1, 1B, 2:
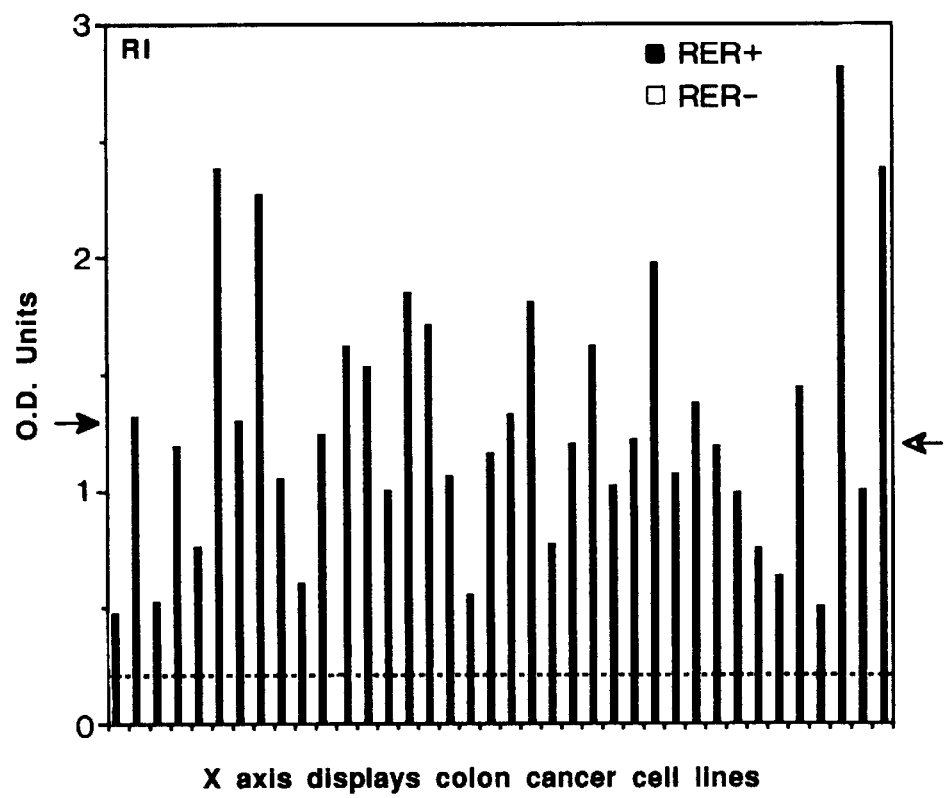
FIG. 2 shows RII transcript expression in colon cancer xenografts measured by RNase protection assay.
Figure 2:
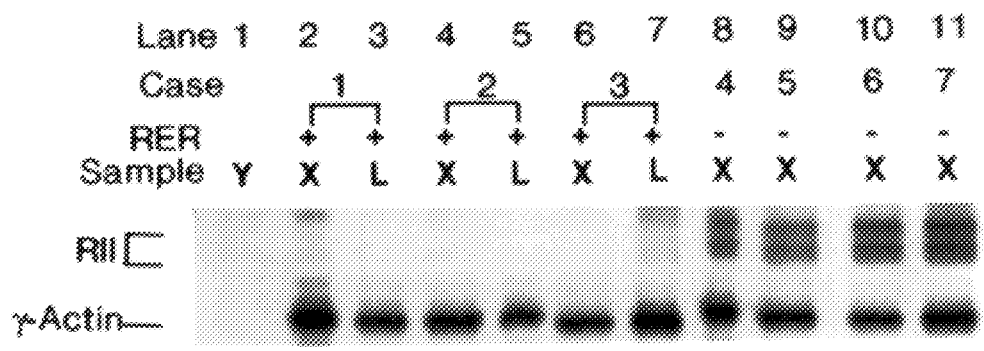

RNase protection assays were used to measure expression of RII and γ-actin transcripts in xenografts (labeled X) established from different human colon tumors. FIG. 2 shows the results for seven of these. Lanes labeled "L" contain samples from immortal cell lines established from the same tumors as the xenografts and are shown for comparison of RII expression. A control reaction displays the protection pattern generated by yeast tRNA (labeled Y).

RII transcripts were absent in 100% (3 of 3) of RER$^+$ xenografts (FIG. 2, xenografts 1–3), but were present at high levels in 93% (25 of 27) of RER$^-$ xenografts (FIG. 2, xenografts 4–7). Moreover, absence of RII transcript in the three RER$^+$ xenografts was the same result observed previously in the three RER$^+$ immortalized cell lines established from the same tumors. Loss of RII transcript was thus not an artifact of cell culture of the cell lines.

Example 3
Absence of TGF-β binding activity

To assay for expression of cell surface TGF-β receptors, we performed cross-linking experiments with $^{125}$I-labeled TGF-β. Cell surface TGF-β receptors were labeled by cross-linking to $^{125}$I-labeled human TGF-β1 as described in Sun, L., et al., 1994 (J. Biol. Chem., 269:26449). Labeled receptors were resolved by SDS-polyacrylamide gel electrophoresis and visualized by autoradiography. There was no detectable $^{125}$I-TGF-β binding to any of eight tested RER$^+$ cell lines with reduced amounts of RII transcript (FIG. 3). The absence of RI surface receptors in these lines (FIG. 3) is consistent with previous reports that RII receptor is required for TGF-β binding to RI (Wrana, J., et al., 1992, Cell, 71:1003; Sun, L., et al., 1994, J. Biol Chem., 269:26449). A third TGF-β receptor (RIII) is expressed in most RER$^+$ and RER$^-$ cell lines (FIG. 3), but is likely without functional consequence, as it is thought to function only in the presentation of ligand to RI and RII (L ópez-Casillas, et al., 1993, Cell, 73:1435).

Example 4
Inactivating Mutations of RII

The RI and RII cell surface receptors were also undetectable in VACO481 cells, one of the two RER$^+$ cases with normal amounts of RI and RII transcripts. Although mutations in RII abolish TGF-β binding to both RI and RII, mutations in RI apparently do not affect TGF-β binding to RII (Wrana, J., et al., 1992, Cell, 71:1003; Boyd, et al., 1989, J. Biol. Chem., 264:2272; Laiho, et al., 1991, ibid., 266:9108; Laiho, et al., 1990, ibid., 265:18518). The absence from VACO481 cells of both RI and RII cell surface receptors would thus be most easily explained by an RII mutation.

The presence of an RII mutation was initially suggested by the results of an in vitro transcription-translation assay. The mutation was confirmed by sequence analysis of complete VACO481 RII cDNA. RII was cloned from complementary DNA (cDNA) using the polymerase chain reaction (RT-PCR). The PCR product was ligated into the pCRII cloning vector (Invitrogen), and the DNA sequences of pooled or individual RII clones determined. The wild-type RII sequence we used as a reference is that updated as GenBank accession #M85079.

Sequence analysis of VACO481 RII cDNA revealed a GT insertion into a 6 base pair (bp) GTGTGT repeat at nucleotides 1931 to 1936 (FIG. 4), and the absence of any normal sequence. The resulting frameshift is predicted to substitute a highly basic, 29-amino-acid COOH-terminus for the slightly acidic 33-amino-acid wild-type COOH-terminus. The predicted COOH-terminal sequence of the VACO481 RII mutant, beginning with Val 534 is: ValTrpGlnAsnAla-SerValSerTrpSerIleTrpThrGly-SerArgGlyGlyAlaAlaArgArgArgPheLeuL ysThrAlaPro SEQ ID NO:7. Sequence changes (which we presume to be polymorphisms because they were present in both the VACO481 tumor and the matched normal tissue) included a C to T change at nucleotide 1651, (converting Ala 439 to Val), and an A to C change at nucleotide 2040 in the 3' untranslated region. Conceivably, this mutation could alter RII conformation, stability, and/or ability to interact with other proteins required for receptor function. The same RII frameshift mutation was also detected in the primary colon tumor from which the VACO481 cell line was established, but not in normal colon tissue from the same patient, indicating the mutation was somatic.

Figure 4:
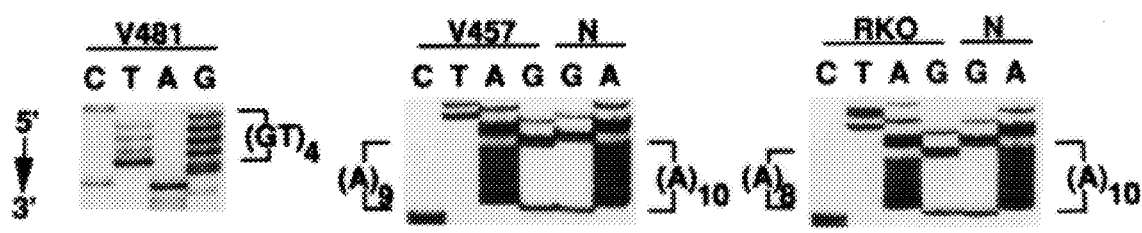
FIG. 4 shows mutant RII sequences in RER+ cell lines. Mutant sequences shown are: VACO481, insertion of GT at wild-type nucleotides 1931–1936; VACO457, one base deletion at wild-type nucleotides 709–718; RKO, two base pair deletion at wild-type nucleotides 709–718. VACO cell lines are designated by the prefix V. The wild-type polyadenine sequence (bp 709–718) obtained from normal tissue is displayed in lanes labeled N.

Frameshift mutations located in 5' regions of mRNA transcripts have been associated with decreased message stability. To search for this type of mutation, we sequenced the 5' portion of the RII cDNA from seven additional RER$^+$ cell lines in which RII transcripts, though markedly reduced, could be recovered by RT-PCR. In each of these cell lines an RII frameshift mutation was found. These mutations were all located within a sequence of ten repeating adenines (nucleotides 709 to 718) which was found shortened by either one base (five cell lines) or two bases (two cell lines) (FIG. 4). RII mutations, detected in three of the cell lines, were also detected in the antecedent patients' colon tumors or in primary xenografts of these tumors. In two cases the mutations were additionally established to be absent in these patients' normal tissues. Compared to wild-type RII (567 amino-acids), the one and two base pair deletions within the poly-adenine tract are predicted to encode inactive truncated receptors of 161 amino-acids and 129 amino-acids, respectively. RII inactivation was thus demonstrated in ten of eleven RER+ cell lines studied by finding RII gene mutations and/or absent cell surface RII, accompanied, in most cases, by low levels of RII transcript. Another RII mutation is a point mutation of G to A at nucleotide 1899 of the Genbank sequence for RII, resulting in substitution of Asn for Asp 522, which occurs in VACO8, a non-RER colon cancer cell line of mutator phenotype with inactive RII.

Example 5
In active RII correlates with RER+ tumors

In contrast to RER+ colon cell lines, only a minority of RER⁻ cell lines showed inactivation of TGF-β receptors. RER⁻ cell lines demonstrated RI and RII transcripts in 90% (24 of 27) (FIG. 1), RI and RII cell surface receptors in 86% (6 of 7) (FIG. 2), and growth inhibition by TGF-β in 100% (5 of 5) of samples studied (Hoosein, N., et al., 1989, *Exp. Cell Res.,* 181:442).

RER+ samples (cell lines and xenografts) in this study were derived from predominantly right-sided (eight of nine evaluable), mostly metastatic (five of nine evaluable) colon cancers. However, RER⁻ samples also included 17 representing right-sided colon cancers (none with RII loss) and 32 representing metastatic colon cancers (only two with RII loss). Thus, loss of RII is characteristic of a cancer's RER phenotype, rather than its site of origin or clinical stage.

Also included among our RER+ samples were two cell lines established from familial colon cancers [hereditary nonpolyposis colorectal cancer, HNPCC], six from sporadic colon cancers (Aaltonen, L., et a l., 1993, *Science,* 260:812; Ionov, et al., 1993, *Nature,* 363:558; Thibodeau, et al., 1993, *Science ,* 260:816; Kim, et al., 1994, *Am. J. Pathol.,* 145:148), five cell lines bearing mutations in a known mismatch repair gene, and four bearing only wild-type versions of these genes (Liu, B., et al., 1995, *Nature Genet.,* 9:48; Papadopoulos, N., et al., 1994, *Science,* 263:1625; Bronner, C., et al., 1994, *Nature,* 17:258; Fishel, R., et al., 1993, *Cell,* 75:1027; Leach, F., et al., 1993, ibid., 75:1215; Nicolaides, N., et al., 1994, *Nature,* 371:75). The type II TGF-β receptor is thus a target for inactivation in each of the currently identified subsets of RER+ colon cancer.

Example 6
Inactivation of R2 Detected in Estrogen Receptor Positive (ER+) Breast Cancers We have demonstrated absence of functional RII in a particular human breast cancer cell line, MCF-7, by demonstrating absence of detectable RII mRNA transcripts, by demonstrating absence of cell surface RII protein able to bind radio-labeled TGF-β, and by demonstrating absence of a TGF-β functional response (absence of TGF-β induced growth inhibition) (Sun, et al., 1994, incorporated herein by reference). Using the methods outlined in Sun, et al., this observation has been extended to show that a substantial subset of human breast cancers lack functional RII, and that lack of functional RII is particularly characteristic of breast cancers which are positive for presence of the estrogen receptor (ER+).

TABLE 1

RII Inactivation In Human Breast Cancer Cell Lines

| Name | ER | RII mRNA | TGF-β Binding To RII | TGF-β Responsive |
|---|---|---|---|---|
| MCF7 | + | − | − | − |
| BT-20 | + | − | − | − |
| ZR-75 | + | − | − | − |
| T-47D | + | − | − | − |
| MDA-MB-231 | − | + | + | + |
| Hs578T | − | + | + | + |

RII inactivation thus contributes to tumor progression in ER+ breast cancer.

For purposes of clarity of understanding, the foregoing invention has been described in some detail by way of illustration and example in conjunction with specific embodiments, although other aspects, advantages and modifications will be apparent to those skilled in the art to which the invention pertains. In particular, modifications of the strategies outlined above for cancer detection, diagnosis, prognosis, and treatment of tumors with absent (inactive) RII as required by the specific mode of RII inactivation in these tumors will be apparent to those skilled in the art. The foregoing description and examples are intended to illustrate, but not limit the scope of the invention. Modifications of the above-described modes for carrying out the invention that are apparent to persons of skill in medicine, immunology, hybridoma technology, pharmacology, and/or related fields are intended to be within the scope of the invention, which is limited only by the appended claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

We claim:

1. A method to aid in predicting prognosis of a cancer patient comprising determining the quantity of functional type II receptor for TGFβ (RII) in cells from tumor tissue of the patient, and comparing the quantity of functional RII in tumor cells to the quantity of functional RII in non-neoplastic cells of the patient, reduced quantity of functional RII in the tumor cells being due to replication errors (RER phenotype) and being indicative of altered prognosis.

2. The method of claim 1, wherein the patient is a colon cancer patient.

3. A method to aid in classifying tumor cell phenotype in a patient comprising determining the presence or absence of functional RII receptor for TGFβ in tumor tissue from the patient, the absence of functional RII being indicative of carcinoma with replication errors (RER phenotype).

4. The method of claim 3, wherein the tumor tissue is selected from the group consisting of colon cancer, endometrial cancer, ovarian cancer, gastric cancer, and pancreatic cancer.

5. A method to aid in classifying tumor cell phenotype comprising determining, in a sample containing cells or extract of cells of the tumor, presence or absence of a nucleotide sequence encoding a mutant form of TGFβ receptor RII, wherein the mutation is selected from the group consisting of a two base pair insertion of GT which occurs in a six base pair repeat sequence GTGTGT at nucleotides 1931–1936 of the normal RII sequence, insertion or deletion of one A base pair from a ten base pair poly A sequence at nucleotides 709 to 718 of the normal RII sequence, and insertion or deletion of two A base pairs from a ten base pair poly A sequence at nucleotides 709 to 718 of the normal RII sequence, the presence of the nucleotide sequence encoding a mutant form of TGFβ receptor RII being indicative of carcinoma with replication errors (RER phenotype).

6. The method of claim 5, wherein presence of the nucleotide sequence encoding a mutant form of TGFβ receptor RII is determined by detection of binding of antibody specifically immunoreactive with mutant RII to mutant RII protein expressed by the cells from the nucleotide sequence, or detection of DNA or RNA sequences encoding the mutant form of RII.

7. A method to aid in diagnosing cancer in a patient comprising determining the presence or absence of functional RII receptor for TGFβ in tissue from the patient, the absence of functional RII being due to replication errors (RER phenotype) and being indicative of tumor tissue or precancerous lesions in the patient.

8. The method of claim 7, wherein absence of functional RII is determined by detecting a mutant form of RII in tissue from the patient.

9. The method of claim 8, wherein the mutant form of RII has a sequence corresponding to RII cDNA altered by a mutation selected from the group consisting of a two base pair insertion of GT which occurs in a six base pair repeat sequence GTGTGT at nucleotides 1931–1936 of the normal RII sequence, insertion or deletion of one A base pair from a ten base pair poly A sequence at nucleotides 709 to 718 of the normal RII sequence, and insertion or deletion of two A base pairs from a ten base pair poly A sequence at nucleotides 709 to 718 of the normal RII sequence.

10. A screening method to aid in diagnosing genetic susceptibility to cancer in a patient comprising determining the presence or absence of mutant forms of RII receptor for TGFβ in a sample from the patient, the presence of mutant forms of RII being due to replication errors (RER phenotype) and being indicative of genetic susceptibility to cancer in the patient.

11. The screening method of claim 10, wherein the mutant forms of RII have a sequence corresponding to RII cDNA altered by a mutation selected from the group consisting of a two base pair insertion of GT which occurs in a six base pair repeat sequence GTGTGT at nucleotides 1931–1936 of the normal RII sequence, insertion or deletion of one A base pair from a ten base pair poly A sequence at nucleotides 709 to 718 of the normal RII sequence, and insertion or deletion of two A base pairs from a ten base pair poly A sequence at nucleotides 709 to 718 of the normal RII sequence.

12. The screening method of claim 11, wherein the presence of RII mutant forms is detected by immunoassay.

13. The screening method of claim 11, wherein the sample is a biological fluid selected from the group consisting of serum, plasma, effusions, ascites, urine, stool, cerebrospinal fluid, semen, breast aspirates and fluids of ovarian origin.

14. An assay for detecting mutation of type II receptor for TGFβ (RII) comprising determining, in a biological sample, presence of a nucleotide sequence encoding a mutant form of TGFβ receptor RII, wherein the mutant form contains a mutation selected from the group consisting of a two base pair insertion of GT which occurs in a six base pair repeat sequence GTGTGT at nucleotides 1931–1936 of the normal RII sequence, insertion or deletion of one A base pair from a ten base pair poly A sequence at nucleotides 709 to 718 of the normal RII sequence, and insertion or deletion of two A base pairs from a ten base pair poly A sequence at nucleotides 709 to 718 of the normal RII sequence.

15. A method to aid in diagnosing cancer in a patient comprising detecting a mutant RII receptor for TGFβ in a sample of biological fluid from the patient, the presence of mutant RII being indicative of tumor tissue or precancerous lesions in the patient.

16. The method to aid in diagnosing cancer in a patient according to claim 15, wherein detection of said mutant form of RII comprises detecting antibody immunologically reactive with the mutant form of RII in a sample of biological fluid from the patient.

17. The method of claim 15, wherein said antibody immunologically reactive with mutant RII receptor for TGFβ is also immunologically reactive with wild type RII receptor.

18. The method of claim 15, wherein the mutant RII receptor for TGFβ is encoded by a mutant RII nucleotide sequence which contains a mutation selected from the group consisting of a two base pair insertion of GT which occurs in a six base pair repeat sequence GTGTGT at nucleotides 1931–1936 of the normal RII sequence, insertion or deletion of one A base pair from a ten base pair poly A sequence at nucleotides 709 to 718 of the normal RII sequence, insertion or deletion of two A base pairs from a ten base pair poly A sequence at nucleotides 709 to 718 of the normal RII sequence, and a point mutation of G to A at nucleotide 1899 of the normal RII sequence.

19. A method to aid in diagnosing cancer in a patient comprising determining the presence or absence of functional RII receptor for TGFβ in a tissue from the patient by detecting a mutant form of RII having a sequence corresponding to RII cDNA altered by a point mutation of G to A at nucleotide 1899 of the normal RII sequence in tissue from the patient, the absence of functional RII being indicative of tumor tissue or precancerous lesions in the patient.

20. A screening method to aid in diagnosing genetic susceptibility to cancer in a patient comprising determining, in a sample from the patient, the presence or absence of a mutant form of RII receptor for TGFβ having a sequence corresponding to RII cDNA altered by a point mutation of G to A at nucleotide 1899 of the normal RII sequence, the presence of said mutant form of RII being indicative of genetic susceptibility to cancer in the patient.

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 20 base pairs
        ( B ) TYPE: nucleic acid

```
            ( C ) STRANDEDNESS: single
            ( D ) TOPOLOGY: linear ( i i ) MOLECULE TYPE: cDNA ( x i ) SEQUENCE DESCRIPTION: SEQ ID NO:1:

GACCAGTGTG CTTCGTCTGC                                                                    20
```

( 2 ) INFORMATION FOR SEQ ID NO:2:

( i ) SEQUENCE CHARACTERISTICS:
            ( A ) LENGTH: 20 base pairs
            ( B ) TYPE: nucleic acid
            ( C ) STRANDEDNESS: single
            ( D ) TOPOLOGY: linear ( i i ) MOLECULE TYPE: cDNA ( x i ) SEQUENCE DESCRIPTION: SEQ ID NO:2:

```
GCTGGCTTTC CTTGGGTACC                                                                    20
```

( 2 ) INFORMATION FOR SEQ ID NO:3:

( i ) SEQUENCE CHARACTERISTICS:
            ( A ) LENGTH: 34 amino acids
            ( B ) TYPE: amino acid
            ( C ) STRANDEDNESS: single
            ( D ) TOPOLOGY: linear ( i i ) MOLECULE TYPE: peptide ( v ) FRAGMENT TYPE: N-terminal ( x i ) SEQUENCE DESCRIPTION: SEQ ID NO:3:

```
Ser  Leu  Val  Arg  Leu  Ser  Ser  Cys  Val  Pro  Val  Ala  Leu  Met  Ser  Ala
 1                   5                        10                       15

Met  Thr  Thr  Ser  Ser  Ser  Gln  Lys  Asn  Ile  Thr  Pro  Ala  Ile  Leu  Thr
                20                       25                       30

Cys  Cys
```

( 2 ) INFORMATION FOR SEQ ID NO:4:

( i ) SEQUENCE CHARACTERISTICS:
            ( A ) LENGTH: 34 amino acids
            ( B ) TYPE: amino acid
            ( C ) STRANDEDNESS: single
            ( D ) TOPOLOGY: linear ( i i ) MOLECULE TYPE: peptide ( v ) FRAGMENT TYPE: N-terminal ( x i ) SEQUENCE DESCRIPTION: SEQ ID NO:4:

```
Lys  Pro  Gly  Glu  Thr  Phe  Phe  Met  Cys  Ser  Cys  Ser  Ser  Asp  Glu  Cys
 1                   5                        10                       15

Asn  Asp  Asn  Ile  Ile  Phe  Ser  Glu  Glu  Tyr  Asn  Thr  Ser  Asn  Pro  Asp
                20                       25                       30

Leu  Leu
```

( 2 ) INFORMATION FOR SEQ ID NO:5:

( i ) SEQUENCE CHARACTERISTICS:
            ( A ) LENGTH: 30 amino acids
            ( B ) TYPE: amino acid
            ( C ) STRANDEDNESS: single
            ( D ) TOPOLOGY: linear ( i i ) MOLECULE TYPE: peptide ( v ) FRAGMENT TYPE: N-terminal ( x i ) SEQUENCE DESCRIPTION: SEQ ID NO:5:

| Val | Trp | Gln | Asn | Ala | Ser | Val | Ser | Trp | Ser | Ile | Trp | Thr | Gly | Ser | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gly | Ala | Ala | Arg | Arg | Arg | Arg | Phe | Leu | Lys | Thr | Ala | Pro |
|-----|-----|-----|-----|-----|-----|-----|-----|-----|-----|-----|-----|-----|-----|
|     |     |     | 20  |     |     |     |     | 25  |     |     |     |     | 30  |

( 2 ) INFORMATION FOR SEQ ID NO:6:

( i ) SEQUENCE CHARACTERISTICS:
        ( A ) LENGTH: 34 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:6:

| Val | Ala | Glu | Arg | Phe | Ser | Glu | Leu | Glu | His | Leu | Asp | Arg | Leu | Ser | Gly |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Arg | Ser | Cys | Ser | Glu | Glu | Lys | Ile | Pro | Glu | Asp | Gly | Ser | Leu | Asn | Thr |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

Thr Lys ( 2 ) INFORMATION FOR SEQ ID NO:7:

( i ) SEQUENCE CHARACTERISTICS:
        ( A ) LENGTH: 30 amino acids
        ( B ) TYPE: amino acid
        ( C ) STRANDEDNESS: single
        ( D ) TOPOLOGY: linear ( i i ) MOLECULE TYPE: peptide ( v ) FRAGMENT TYPE: N-terminal ( x i ) SEQUENCE DESCRIPTION: SEQ ID NO:7:

| Val | Trp | Gln | Asn | Ala | Ser | Val | Ser | Trp | Ser | Ile | Trp | Thr | Gly | Ser | Arg |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Gly | Gly | Ala | Ala | Arg | Arg | Arg | Arg | Phe | Leu | Lys | Thr | Ala | Pro |
|-----|-----|-----|-----|-----|-----|-----|-----|-----|-----|-----|-----|-----|-----|
|     |     |     | 20  |     |     |     |     | 25  |     |     |     |     | 30  |

( 2 ) INFORMATION FOR SEQ ID NO:8:

( i ) SEQUENCE CHARACTERISTICS:
        ( A ) LENGTH: 2090 base pairs
        ( B ) TYPE: nucleic acid
        ( C ) STRANDEDNESS: single
        ( D ) TOPOLOGY: linear ( i x ) FEATURE:
        ( A ) NAME/KEY: Coding Sequence
        ( B ) LOCATION: 336...2036
        ( D ) OTHER INFORMATION:

( x i ) SEQUENCE DESCRIPTION: SEQ ID NO:8:

| GTTGGCGAGG | AGTTTCCTGT | TTCCCCCGCA | GCGCTGAGTT | GAAGTTGAGT | GAGTCACTCG | 60 |
| CGCGCACGGA | GCGACGACAC | CCCCGCGCGT | GCACCCGCTC | GGGACAGGAG | CCGGACTCCT | 120 |
| GTGCAGCTTC | CCTCGGCCGC | CGGGGGCCTC | CCCGCGCCTC | GCCGGCCTCC | AGGCCCCTCC | 180 |
| TGGCTGGCGA | GCGGGCGCCA | CATCTGGCCC | GCACATCTGC | GCTGCCGGCC | CGGCGCGGGG | 240 |
| TCCGGAGAGG | GCGCGGCGCG | GAGCGCAGCC | AGGGGTCCGG | GAAGGCGCCG | TCCGTGCGCT | 300 |

|  |  |  |  |  |  |  |  |  |  |  |  |  |  | |
|---|---|---|---|---|---|---|---|---|---|---|---|---|---|---|
| GGGGGCTCGG | TCTATGACGA | GCAGCGGGGT | CTGCC | ATG | GGT | CGG | GGG | CTG | CTC | | | | | 353 |
| | | | | Met<br>1 | Gly | Arg | Gly | Leu<br>5 | Leu | | | | | |

| AGG | GGC | CTG | TGG | CCG | CTG | CAC | ATC | GTC | CTG | TGG | ACG | CGT | ATC | GCC | AGC | 401 |
|---|---|---|---|---|---|---|---|---|---|---|---|---|---|---|---|---|
| Arg | Gly | Leu<br>10 | Trp | Pro | Leu | His | Ile | Val<br>15 | Leu | Trp | Thr | Arg | Ile<br>20 | Ala | Ser | |
| ACG | ATC | CCA | CCG | CAC | GTT | CAG | AAG | TCG | GTT | AAT | AAC | GAC | ATG | ATA | GTC | 449 |
| Thr | Ile | Pro<br>25 | Pro | His | Val | Gln | Lys<br>30 | Ser | Val | Asn | Asn | Asp<br>35 | Met | Ile | Val | |
| ACT | GAC | AAC | AAC | GGT | GCA | GTC | AAG | TTT | CCA | CAA | CTG | TGT | AAA | TTT | TGT | 497 |
| Thr | Asp | Asn<br>40 | Asn | Gly | Ala | Val | Lys<br>45 | Phe | Pro | Gln | Leu | Cys<br>50 | Lys | Phe | Cys | |
| GAT | GTG | AGA | TTT | TCC | ACC | TGT | GAC | AAC | CAG | AAA | TCC | TGC | ATG | AGC | AAC | 545 |
| Asp<br>55 | Val | Arg | Phe | Ser | Thr<br>60 | Cys | Asp | Asn | Gln | Lys<br>65 | Ser | Cys | Met | Ser | Asn<br>70 | |
| TGC | AGC | ATC | ACC | TCC | ATC | TGT | GAG | AAG | CCA | CAG | GAA | GTC | TGT | GTG | GCT | 593 |
| Cys | Ser | Ile | Thr | Ser<br>75 | Ile | Cys | Glu | Lys | Pro<br>80 | Gln | Glu | Val | Cys | Val<br>85 | Ala | |
| GTA | TGG | AGA | AAG | AAT | GAC | GAG | AAC | ATA | ACA | CTA | GAG | ACA | GTT | TGC | CAT | 641 |
| Val | Trp | Arg | Lys<br>90 | Asn | Asp | Glu | Asn | Ile<br>95 | Thr | Leu | Glu | Thr | Val<br>100 | Cys | His | |
| GAC | CCC | AAG | CTC | CCC | TAC | CAT | GAC | TTT | ATT | CTG | GAA | GAT | GCT | GCT | TCT | 689 |
| Asp | Pro | Lys<br>105 | Leu | Pro | Tyr | His | Asp<br>110 | Phe | Ile | Leu | Glu | Asp<br>115 | Ala | Ala | Ser | |
| CCA | AAG | TGC | ATT | ATG | AAG | GAA | AAA | AAA | AAG | CCT | GGT | GAG | ACT | TTC | TTC | 737 |
| Pro | Lys<br>120 | Cys | Ile | Met | Lys | Glu<br>125 | Lys | Lys | Lys | Pro | Gly<br>130 | Glu | Thr | Phe | Phe | |
| ATG | TGT | TCC | TGT | AGC | TCT | GAT | GAG | TGC | AAT | GAC | AAC | ATC | ATC | TTC | TCA | 785 |
| Met<br>135 | Cys | Ser | Cys | Ser | Ser<br>140 | Asp | Glu | Cys | Asn | Asp<br>145 | Asn | Ile | Ile | Phe | Ser<br>150 | |
| GAA | GAA | TAT | AAC | ACC | AGC | AAT | CCT | GAC | TTG | TTG | CTA | GTC | ATA | TTT | CAA | 833 |
| Glu | Glu | Tyr | Asn | Thr<br>155 | Ser | Asn | Pro | Asp | Leu<br>160 | Leu | Leu | Val | Ile | Phe<br>165 | Gln | |
| GTG | ACA | GGC | ATC | AGC | CTC | CTG | CCA | CCA | CTG | GGA | GTT | GCC | ATA | TCT | GTC | 881 |
| Val | Thr | Gly | Ile<br>170 | Ser | Leu | Leu | Pro | Pro<br>175 | Leu | Gly | Val | Ala | Ile<br>180 | Ser | Val | |
| ATC | ATC | ATC | TTC | TAC | TGC | TAC | CGC | GTT | AAC | CGG | CAG | CAG | AAG | CTG | AGT | 929 |
| Ile | Ile | Ile<br>185 | Phe | Tyr | Cys | Tyr | Arg<br>190 | Val | Asn | Arg | Gln | Gln<br>195 | Lys | Leu | Ser | |
| TCA | ACC | TGG | GAA | ACC | GGC | AAG | ACG | CGG | AAG | CTC | ATG | GAG | TTC | AGC | GAG | 977 |
| Ser | Thr<br>200 | Trp | Glu | Thr | Gly | Lys<br>205 | Thr | Arg | Lys | Leu | Met<br>210 | Glu | Phe | Ser | Glu | |
| CAC | TGT | GCC | ATC | ATC | CTG | GAA | GAT | GAC | CGC | TCT | GAC | ATC | AGC | TCC | ACG | 1025 |
| His<br>215 | Cys | Ala | Ile | Ile | Leu<br>220 | Glu | Asp | Asp | Arg | Ser<br>225 | Asp | Ile | Ser | Ser | Thr<br>230 | |
| TGT | GCC | AAC | AAC | ATC | AAC | CAC | AAC | ACA | GAG | CTG | CTG | CCC | ATT | GAG | CTG | 1073 |
| Cys | Ala | Asn | Asn | Ile<br>235 | Asn | His | Asn | Thr | Glu<br>240 | Leu | Leu | Pro | Ile | Glu<br>245 | Leu | |
| GAC | ACC | CTG | GTG | GGG | AAA | GGT | CGC | TTT | GCT | GAG | GTC | TAT | AAG | GCC | AAG | 1121 |
| Asp | Thr | Leu | Val<br>250 | Gly | Lys | Gly | Arg | Phe<br>255 | Ala | Glu | Val | Tyr | Lys<br>260 | Ala | Lys | |
| CTG | AAG | CAG | AAC | ACT | TCA | GAG | CAG | TTT | GAG | ACA | GTG | GCA | GTC | AAG | ATC | 1169 |
| Leu | Lys | Gln | Asn<br>265 | Thr | Ser | Glu | Gln | Phe<br>270 | Glu | Thr | Val | Ala | Val<br>275 | Lys | Ile | |
| TTT | CCC | TAT | GAG | GAG | TAT | GCC | TCT | TGG | AAG | ACA | GAG | AAG | GAC | ATC | TTC | 1217 |
| Phe | Pro<br>280 | Tyr | Glu | Glu | Tyr | Ala<br>285 | Ser | Trp | Lys | Thr | Glu<br>290 | Lys | Asp | Ile | Phe | |
| TCA | GAC | ATC | AAT | CTG | AAG | CAT | GAG | AAC | ATA | CTC | CAG | TTC | CTG | ACG | GCT | 1265 |
| Ser<br>295 | Asp | Ile | Asn | Leu | Lys<br>300 | His | Glu | Asn | Ile | Leu<br>305 | Gln | Phe | Leu | Thr | Ala<br>310 | |

| | | | | | | | | | | | | | | | | |
|---|---|---|---|---|---|---|---|---|---|---|---|---|---|---|---|---|
|GAG|GAG|CGG|AAG|ACG|GAG|TTG|GGG|AAA|CAA|TAC|TGG|CTG|ATC|ACC|GCC|1313|
|Glu|Glu|Arg|Lys|Thr 315|Glu|Leu|Gly|Lys|Gln 320|Tyr|Trp|Leu|Ile|Thr 325|Ala| |
|TTC|CAC|GCC|AAG|GGC|AAC|CTA|CAG|GAG|TAC|CTG|ACG|CGG|CAT|GTC|ATC|1361|
|Phe|His|Ala|Lys 330|Gly|Asn|Leu|Gln|Glu 335|Tyr|Leu|Thr|Arg|His 340|Val|Ile| |
|AGC|TGG|GAG|GAC|CTG|CGC|AAG|CTG|GGC|AGC|TCC|CTC|GCC|CGG|GGG|ATT|1409|
|Ser|Trp|Glu 345|Asp|Leu|Arg|Lys|Leu|Gly 350|Ser|Ser|Leu|Ala|Arg 355|Gly|Ile| |
|GCT|CAC|CTC|CAC|AGT|GAT|CAC|ACT|CCA|TGT|GGG|AGG|CCC|AAG|ATG|CCC|1457|
|Ala|His 360|Leu|His|Ser|Asp|His 365|Thr|Pro|Cys|Gly|Arg 370|Pro|Lys|Met|Pro| |
|ATC|GTG|CAC|AGG|GAC|CTC|AAG|AGC|TCC|AAT|ATC|CTC|GTG|AAG|AAC|GAC|1505|
|Ile 375|Val|His|Arg|Asp 380|Leu|Lys|Ser|Ser|Asn 385|Ile|Leu|Val|Lys|Asn|Asp 390| |
|CTA|ACC|TGC|TGC|CTG|TGT|GAC|TTT|GGG|CTT|TCC|CTG|CGT|CTG|GAC|CCT|1553|
|Leu|Thr|Cys|Cys|Leu 395|Cys|Asp|Phe|Gly|Leu 400|Ser|Leu|Arg|Leu|Asp 405|Pro| |
|ACT|CTG|TCT|GTG|GAT|GAC|CTG|GCT|AAC|AGT|GGG|CAG|GTG|GGA|ACT|GCA|1601|
|Thr|Leu|Ser|Val 410|Asp|Asp|Leu|Ala|Asn 415|Ser|Gly|Gln|Val|Gly 420|Thr|Ala| |
|AGA|TAC|ATG|GCT|CCA|GAA|GTC|CTA|GAA|TCC|AGG|ATG|AAT|TTG|GAG|AAT|1649|
|Arg|Tyr|Met 425|Ala|Pro|Glu|Val|Leu 430|Glu|Ser|Arg|Met|Asn 435|Leu|Glu|Asn| |
|GCT|GAG|TCC|TTC|AAG|CAG|ACC|GAT|GTC|TAC|TCC|ATG|GCT|CTG|GTG|CTC|1697|
|Ala|Glu 440|Ser|Phe|Lys|Gln|Thr 445|Asp|Val|Tyr|Ser|Met 450|Ala|Leu|Val|Leu| |
|TGG|GAA|ATG|ACA|TCT|CGC|TGT|AAT|GCA|GTG|GGA|GAA|GTA|AAA|GAT|TAT|1745|
|Trp 455|Glu|Met|Thr|Ser|Arg 460|Cys|Asn|Ala|Val|Gly 465|Glu|Val|Lys|Asp|Tyr 470| |
|GAG|CCT|CCA|TTT|GGT|TCC|AAG|GTG|CGG|GAG|CAC|CCC|TGT|GTC|GAA|AGC|1793|
|Glu|Pro|Pro|Phe|Gly 475|Ser|Lys|Val|Arg|Glu 480|His|Pro|Cys|Val|Glu 485|Ser| |
|ATG|AAG|GAC|AAC|GTG|TTG|AGA|GAT|CGA|GGG|CGA|CCA|GAA|ATT|CCC|AGC|1841|
|Met|Lys|Asp|Asn 490|Val|Leu|Arg|Asp|Arg 495|Gly|Arg|Pro|Glu|Ile 500|Pro|Ser| |
|TTC|TGG|CTC|AAC|CAC|CAG|GGC|ATC|CAG|ATG|GTG|TGT|GAG|ACG|TTG|ACT|1889|
|Phe|Trp|Leu 505|Asn|His|Gln|Gly|Ile 510|Gln|Met|Val|Cys|Glu 515|Thr|Leu|Thr| |
|GAG|TGC|TGG|GAC|CAC|GAC|CCA|GAG|GCC|CGT|CTC|ACA|GCC|CAG|TGT|GTG|1937|
|Glu|Cys 520|Trp|Asp|His|Asp|Pro 525|Glu|Ala|Arg|Leu|Thr 530|Ala|Gln|Cys|Val| |
|GCA|GAA|CGC|TTC|AGT|GAG|CTG|GAG|CAT|CTG|GAC|AGG|CTC|TCG|GGG|AGG|1985|
|Ala 535|Glu|Arg|Phe|Ser|Glu 540|Leu|Glu|His|Leu|Asp 545|Arg|Leu|Ser|Gly|Arg 550| |
|AGC|TGC|TCG|GAG|GAG|AAG|ATT|CCT|GAA|GAC|GGC|TCC|CTA|AAC|ACT|ACC|2033|
|Ser|Cys|Ser|Glu|Glu 555|Lys|Ile|Pro|Glu|Asp 560|Gly|Ser|Leu|Asn|Thr 565|Thr| |
|AAA|TAGCTCTTAT|GGGGCAGGCT|GGGCATGTCC|AAAGAGGCTG|CCCCTCTCAC|CAAA| | | | | | | | | |2090|
|Lys| | | | | | | | | | | | | | | | |

( 2 ) INFORMATION FOR SEQ ID NO:9:

( i ) SEQUENCE CHARACTERISTICS:
        ( A ) LENGTH: 567 amino acids
        ( B ) TYPE: amino acid
        ( C ) STRANDEDNESS: single
        ( D ) TOPOLOGY: linear ( i i ) MOLECULE TYPE: protein ( v ) FRAGMENT TYPE: internal ( x i ) SEQUENCE DESCRIPTION: SEQ ID NO:9:

| | | | | | | | | | | | | | | |
|---|---|---|---|---|---|---|---|---|---|---|---|---|---|---|
| Met | Gly | Arg | Gly | Leu | Leu | Arg | Gly | Leu | Trp | Pro | Leu | His | Ile | Val | Leu |
| 1 | | | | 5 | | | | | 10 | | | | | 15 | |
| Trp | Thr | Arg | Ile | Ala | Ser | Thr | Ile | Pro | Pro | His | Val | Gln | Lys | Ser | Val |
| | | | 20 | | | | | 25 | | | | | 30 | | |
| Asn | Asn | Asp | Met | Ile | Val | Thr | Asp | Asn | Gly | Ala | Val | Lys | Phe | Pro | |
| | | 35 | | | | | 40 | | | | 45 | | | | |
| Gln | Leu | Cys | Lys | Phe | Cys | Asp | Val | Arg | Phe | Ser | Thr | Cys | Asp | Asn | Gln |
| | 50 | | | | 55 | | | | | 60 | | | | | |
| Lys | Ser | Cys | Met | Ser | Asn | Cys | Ser | Ile | Thr | Ser | Ile | Cys | Glu | Lys | Pro |
| 65 | | | | | 70 | | | | 75 | | | | | | 80 |
| Gln | Glu | Val | Cys | Val | Ala | Val | Trp | Arg | Lys | Asn | Asp | Glu | Asn | Ile | Thr |
| | | | | 85 | | | | | 90 | | | | | 95 | |
| Leu | Glu | Thr | Val | Cys | His | Asp | Pro | Lys | Leu | Pro | Tyr | His | Asp | Phe | Ile |
| | | | 100 | | | | | 105 | | | | | 110 | | |
| Leu | Glu | Asp | Ala | Ala | Ser | Pro | Lys | Cys | Ile | Met | Lys | Glu | Lys | Lys | Lys |
| | | | 115 | | | | 120 | | | | | 125 | | | |
| Pro | Gly | Glu | Thr | Phe | Phe | Met | Cys | Ser | Cys | Ser | Ser | Asp | Glu | Cys | Asn |
| | 130 | | | | | 135 | | | | | 140 | | | | |
| Asp | Asn | Ile | Ile | Phe | Ser | Glu | Glu | Tyr | Asn | Thr | Ser | Asn | Pro | Asp | Leu |
| 145 | | | | | 150 | | | | | 155 | | | | | 160 |
| Leu | Leu | Val | Ile | Phe | Gln | Val | Thr | Gly | Ile | Ser | Leu | Leu | Pro | Pro | Leu |
| | | | | 165 | | | | | 170 | | | | | 175 | |
| Gly | Val | Ala | Ile | Ser | Val | Ile | Ile | Ile | Phe | Tyr | Cys | Tyr | Arg | Val | Asn |
| | | | 180 | | | | | 185 | | | | | 190 | | |
| Arg | Gln | Gln | Lys | Leu | Ser | Ser | Thr | Trp | Glu | Thr | Gly | Lys | Thr | Arg | Lys |
| | | | 195 | | | | | 200 | | | | | 205 | | |
| Leu | Met | Glu | Phe | Ser | Glu | His | Cys | Ala | Ile | Ile | Leu | Glu | Asp | Asp | Arg |
| | 210 | | | | | 215 | | | | | 220 | | | | |
| Ser | Asp | Ile | Ser | Ser | Thr | Cys | Ala | Asn | Asn | Ile | Asn | His | Asn | Thr | Glu |
| 225 | | | | | 230 | | | | | 235 | | | | | 240 |
| Leu | Leu | Pro | Ile | Glu | Leu | Asp | Thr | Leu | Val | Gly | Lys | Gly | Arg | Phe | Ala |
| | | | | 245 | | | | | 250 | | | | | 255 | |
| Glu | Val | Tyr | Lys | Ala | Lys | Leu | Lys | Gln | Asn | Thr | Ser | Glu | Gln | Phe | Glu |
| | | | 260 | | | | | 265 | | | | | 270 | | |
| Thr | Val | Ala | Val | Lys | Ile | Phe | Pro | Tyr | Glu | Glu | Tyr | Ala | Ser | Trp | Lys |
| | | 275 | | | | | 280 | | | | | 285 | | | |
| Thr | Glu | Lys | Asp | Ile | Phe | Ser | Asp | Ile | Asn | Leu | Lys | His | Glu | Asn | Ile |
| | 290 | | | | | 295 | | | | | 300 | | | | |
| Leu | Gln | Phe | Leu | Thr | Ala | Glu | Glu | Arg | Lys | Thr | Glu | Leu | Gly | Lys | Gln |
| 305 | | | | | 310 | | | | | 315 | | | | | 320 |
| Tyr | Trp | Leu | Ile | Thr | Ala | Phe | His | Ala | Lys | Gly | Asn | Leu | Gln | Glu | Tyr |
| | | | | 325 | | | | | 330 | | | | | 335 | |
| Leu | Thr | Arg | His | Val | Ile | Ser | Trp | Glu | Asp | Leu | Arg | Lys | Leu | Gly | Ser |
| | | | 340 | | | | | 345 | | | | | 350 | | |
| Ser | Leu | Ala | Arg | Gly | Ile | Ala | His | Leu | His | Ser | Asp | His | Thr | Pro | Cys |
| | | 355 | | | | | 360 | | | | | 365 | | | |
| Gly | Arg | Pro | Lys | Met | Pro | Ile | Val | His | Arg | Asp | Leu | Lys | Ser | Ser | Asn |
| | 370 | | | | | 375 | | | | | 380 | | | | |
| Ile | Leu | Val | Lys | Asn | Asp | Leu | Thr | Cys | Cys | Leu | Cys | Asp | Phe | Gly | Leu |
| 385 | | | | | 390 | | | | | 395 | | | | | 400 |
| Ser | Leu | Arg | Leu | Asp | Pro | Thr | Leu | Ser | Val | Asp | Asp | Leu | Ala | Asn | Ser |
| | | | | 405 | | | | | 410 | | | | | 415 | |

-continued

| Gly | Gln | Val | Gly 420 | Thr | Ala | Arg | Tyr | Met 425 | Ala | Pro | Glu | Val | Leu 430 | Glu | Ser |
|---|---|---|---|---|---|---|---|---|---|---|---|---|---|---|---|
| Arg | Met | Asn 435 | Leu | Glu | Asn | Ala | Glu 440 | Ser | Phe | Lys | Gln | Thr 445 | Asp | Val | Tyr |
| Ser | Met 450 | Ala | Leu | Val | Leu | Trp 455 | Glu | Met | Thr | Ser | Arg 460 | Cys | Asn | Ala | Val |
| Gly 465 | Glu | Val | Lys | Asp | Tyr 470 | Glu | Pro | Pro | Phe | Gly 475 | Ser | Lys | Val | Arg | Glu 480 |
| His | Pro | Cys | Val | Glu 485 | Ser | Met | Lys | Asp | Asn 490 | Val | Leu | Arg | Asp | Arg 495 | Gly |
| Arg | Pro | Glu | Ile 500 | Pro | Ser | Phe | Trp | Leu 505 | Asn | His | Gln | Gly | Ile 510 | Gln | Met |
| Val | Cys | Glu 515 | Thr | Leu | Thr | Glu | Cys 520 | Trp | Asp | His | Asp | Pro 525 | Glu | Ala | Arg |
| Leu | Thr 530 | Ala | Gln | Cys | Val | Ala 535 | Glu | Arg | Phe | Ser | Glu 540 | Leu | Glu | His | Leu |
| Asp 545 | Arg | Leu | Ser | Gly | Arg 550 | Ser | Cys | Ser | Glu | Glu 555 | Lys | Ile | Pro | Glu | Asp 560 |
| Gly | Ser | Leu | Asn | Thr 565 | Thr | Lys | | | | | | | | | |